United States Patent
Cunningham et al.

(10) Patent No.: US 6,869,923 B1
(45) Date of Patent: Mar. 22, 2005

(54) PERFUME COMPOSITIONS

(75) Inventors: Philip Andrew Cunningham, Newcastle upon Tyne (GB); Michael Green, Newcastle upon Tyne (GB); Allan Campbell McRitchie, Whitley Bay (GB)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/701,803

(22) PCT Filed: Jun. 4, 1999

(86) PCT No.: PCT/IB99/01028

§ 371 (c)(1),
(2), (4) Date: Dec. 1, 2000

(87) PCT Pub. No.: WO99/65458

PCT Pub. Date: Dec. 23, 1999

(30) Foreign Application Priority Data

Jun. 15, 1998  (EP) ............................................ 98870137

(51) Int. Cl.⁷ ................................................. A61K 7/46
(52) U.S. Cl. .............................. 512/4; 512/1; 510/101
(58) Field of Search ......................... 512/4, 1; 510/101

(56) References Cited

U.S. PATENT DOCUMENTS

| | | | |
|---|---|---|---|
| 3,971,852 A | 7/1976 | Brenner et al. | ............ 426/103 |
| 5,354,559 A | 10/1994 | Morehouse | ................. 424/488 |
| 5,500,137 A | 3/1996 | Bacon et al. | |
| 5,500,138 A * | 3/1996 | Bacon et al. | ............... 510/102 |
| 5,500,154 A | 3/1996 | Bacon et al. | |
| 5,540,853 A | 7/1996 | Trinh et al. | |
| 5,652,206 A | 7/1997 | Bacon et al. | |
| 5,668,094 A | 9/1997 | Bacon et al. | |
| 5,780,404 A | 7/1998 | Bacon et al. | |
| 5,833,999 A | 11/1998 | Trinh et al. | |
| 5,849,310 A | 12/1998 | Trinh et al. | |
| 5,876,755 A | 3/1999 | Perring et al. | |
| 6,001,789 A | 12/1999 | Trinh et al. | |
| 6,086,903 A | 7/2000 | Trinh et al. | |
| 6,143,707 A | 11/2000 | Trinh et al. | |
| 6,194,362 B1 | 2/2001 | Trinh et al. | |
| 6,458,754 B1 * | 10/2002 | Velazquez et al. | .......... 510/441 |

FOREIGN PATENT DOCUMENTS

| | | | |
|---|---|---|---|
| CA | 2206458 | 12/1994 | |
| CA | 2245959 | 2/1996 | |
| GB | 2311296 A | 9/1997 | |
| WO | WO 97/06235 | 2/1997 | ............ C11D/3/50 |
| WO | WO 99/55819 A1 | 11/1999 | |

* cited by examiner

Primary Examiner—Robert J. Warden, Sr.
Assistant Examiner—Monique T. Cole
(74) Attorney, Agent, or Firm—James F. McBride; Kim W. Zerby; Steve W. Miller

(57) ABSTRACT

The present invention relates to a perfume composition for delivery of high impact accord perfume ingredients, encapsulated embodiments of such compositions and their use in laundry and cleaning applications.

15 Claims, No Drawings

PERFUME COMPOSITIONS

CROSS REFERENCE TO RELATED APPLICATIONS

This application is a national stage entry under 35 U.S.C. § 371 of PCT/IB99/01028, filed Jun. 4, 1999, which claims priority to EP 98870137.1 filed Jun. 15, 1998.

TECHNICAL FIELD OF THE INVENTION

The present invention relates to perfume compositions for delivery of high impact accord (HIA) perfume ingredients. In particular, the present invention relates to said encapsulated perfume composition and their use in laundry and cleaning products.

BACKGROUND OF THE INVENTION

Most consumers have come to expect scented detergent products and to expect that fabrics and other items which have been laundered with these products also have a pleasing fragrance. Further, perfumes by their ability to provide an olfactory aesthetic benefit can serve as a signal of cleanliness.

Therefore, it is desirable and commercially beneficial to add perfume materials to such products. Perfume additives make laundry compositions more aesthetically pleasing to the consumer, and in some cases the perfume imparts a pleasant fragrance to fabrics treated therewith. However, the amount of perfume carry-over from an aqueous laundry bath onto fabrics is often marginal. Industry, therefore, has long searched for an effective perfume delivery system for use in detergent products which provides long-lasting, storage-stable fragrance to the product, as well as fragrance which masks wet solution odor during use and provides fragrance to the laundered items.

Detergent compositions which contain perfume mixed with or sprayed onto the compositions are well known from commercial practice. Because perfumes are made of a combination of volatile compounds, perfume can be continuously emitted from simple solutions and dry mixes to which the perfume has been added. Various techniques have been developed to hinder or delay the release of perfume from compositions so that they will remain aesthetically pleasing for a longer length of time. To date, however, few of the methods deliver significant fabric and wet solution odor benefits after prolonged storage of the product.

Moreover, there has been a continuing search for methods and compositions which will effectively and efficiently deliver perfume into an aqueous laundry bath providing a relatively strong scent in the headspace just above the solution, then from the laundry bath onto fabric surfaces. Various methods of perfume delivery have been developed involving protection of the perfume through the wash cycle, with subsequent release of the perfume onto fabrics.

One method for delivery of perfume in the wash cycle involves combining the perfume with an emulsifier and water-soluble polymer, forming the mixture into particles, and adding them to a laundry composition, as is described in U.S. Pat. No. 4,209,417, Whyte, issued Jun. 24, 1980; U.S. Pat. No. 4,339,356, Whyte, issued Jul. 13, 1982; and U.S. Pat. No. 3,576,760, Gould et al, issued Apr. 27, 1971.

However, even with the substantial work done by industry in this area, a need still exists for a simple, more efficient and effective perfume delivery system which can be mixed with laundry compositions to provide initial and lasting perfume benefits to fabrics which have been treated with the laundry product.

Another problem in providing perfumed products is the odor intensity associated with the products, especially high density granular detergent compositions. As the density and concentration of the detergent composition increase, the odor from the perfume components can become undesirably intense. A need therefore exists for a perfume delivery system which substantially releases the perfume odor during use and thereafter from the dry fabric, but which does not provide an overly- intensive odor to the product itself.

Still another problem in providing perfumes for products is the odor intensity on fabrics. Indeed, nowadays with the trends for consumer to have mixed laundering such as synthetic and cotton. it is desirable to provide increased odour on both synthetic and cotton fabrics. It has now been found that odor intensity although good on wet fabric is somewhat lessened on dry fabrics, in particular dry cotton fabrics. Accordingly, a need exists for a perfume delivery system which substantially releases the perfume odor during use and thereafter from the dry fabric whatever the type of fabrics treated therewith.

By the present invention, it has now been discovered that perfume ingredients, can be selected based on specific selection criteria to maximize impact during and/or after the wash process, while minimizing the amount of ingredients needed in total to achieve a consumer noticeable benefit. Such compositions are desirable not only for their consumer noticeable benefits (e.g., odor aesthetics), but also for their potentially reduced cost through efficient use of lesser amounts of ingredients.

The present invention solves the long-standing need for a simple, effective, storage-stable delivery system which provides surprising odor benefits (especially odor benefits on fabrics) after the laundering process. Further, encapsulated perfume-containing compositions have reduced product odor during storage of the composition.

SUMMARY OF THE INVENTION

The present invention is a perfume composition comprising:

a)-at least 10% by weight of at least one High Impact Accord ("HIA") perfume ingredient of Class 1, the Class 1 perfume ingredient having (1) a boiling point at 760 mm Hg, of 275° C. or lower, (2) a calculated CLogP of at least 2.0, and (3) an odor detection threshold ("ODT") less than or equal to 50 ppb; and b)-at least 30% by weight of at least one High Impact Accord ("HIA") perfume ingredient of Class 2, the Class 2 perfume ingredient having (1) a boiling point at 760 mm Hg, of greater than 275° C., (2) a calculated CLogP of at least 4.0, and (3) an odor detection threshold ("ODT") less than or equal to 50 ppb.

In a preferred embodiment, the perfume composition is present in an encapsulated form.

In another aspect of the invention, there is provided a laundry and cleaning composition comprising the perfume composition of the invention.

DETAILED DESCRIPTION OF THE INVENTION

Perfume Composition

A perfume composition as defined hereinafter is an essential component of the invention. The perfume composition according to the invention comprises at least two class of perfume ingredients: a first High Impact Accord ("HIA") perfume ingredients, the first perfume ingredient having (1) a boiling point at 760 mm Hg, of 275° C. or lower, (2) a calculated CLogP of at least 2.0, and (3) an odor detection threshold ("ODT") less than or equal to 50 ppb, and a second High Impact Accord ("HIA") perfume ingredients, the second perfume ingredient having (1) a boiling point at 760 mm Hg, of greater than 275° C., (2) a calculated CLogP of at least 4.0, and (3) an odor detection threshold ("ODT") less than or equal to 50 ppb.

The HIA perfume ingredients are characterized by their respective boiling point (B.P.), octanol/water partition coefficient (P) and odor detection threshold ("ODT").

The octanol/water partition coefficient of a perfume ingredient is the ratio between its equilibrium concentrations in octanol and in water.

The boiling points of many perfume ingredients, at standard 760 mm Hg are given in, e.g., "Perfume and Flavor Chemicals (Aroma Chemicals)," Steffen Arctander, published by the author, 1969, incorporated herein by reference.

The logP values of many perfume ingredients have been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo ( cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention.

Odor detection thresholds are determined using a gas chromatograph. The gas chromatograph is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and hence the concentration of material. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability.

The necessary amount of analyte is injected onto the column to achieve a 50 ppb concentration at the detector. Typical gas chromatograph parameters for determining odor detection thresholds are listed below.

GC: 5890 Series II with FID detector
7673 Autosampler
Column: J&W Scientific DB-1
Length 30 meters ID 0.25 mm film thickness 1 micron
Method:
Split Injection: 17/1 split ratio
Autosampler: 1.13 microliters per injection
Column Flow: 1.10 mL/minute
Air Flow: 345 mL/minute
Inlet Temp. 245° C.
Detector Temp. 285° C.
Temperature Information
Initial Temperature: 50° C.
Rate: 5 C/minute
Final Temperature: 280° C.
Final Time: 6 minutes
Leading assumptions:
  (i) 12 seconds per sniff
  (ii) GC air adds to sample dilution A-High Impact Accord ("HIA") Perfume Ingredients of Class 1

For this first class of perfume ingredients, each Class 1 HIA perfume ingredient of this invention has a B.P., determined at the normal, standard pressure of about 760 mm Hg, of 275° C. or lower, an octanol/water partition coefficient P of about 2,000 or higher, and an ODT of less than or equal to 50 parts per billion (ppb). Since the partition coefficients of the preferred perfume ingredients of this invention have high values, they are more conveniently given in the form of their logarithm to the base 10, logP. Thus the preferred perfume ingredients of this invention have ClogP of about 2 and higher.

Table 1 gives some non-limiting examples of HIA perfume ingredients of Class 1.

TABLE 1

HIA Perfume Ingredients of Class 1
HIA Ingredient of Class 1

4-(2,2,6-Trimethylcyclohex-1-enyl)-2-but-en-4-one
2,4-Decadienoic acid, ethyl ester (E,Z)-
6-(and -8) isopropylquinoline
Acetaldehyde phenylethyl propyl acetal
Acetic acid, (2-methylbutoxy)-, 2-propenyl ester
Acetic acid, (3-methylbutoxy)-, 2-propenyl ester
2,6,10-Trimethyl-9-undecenal
Glycolic acid, 2-pentyloxy-, allyl ester
Hexanoic acid, 2-propenyl ester
1-Octen-3-ol
trans-Anethole
iso butyl (z)-2-methyl-2-butenoate
Anisaldehyde diethyl acetal
Benzenepropanal, 4-(1,1-dimethylethyl)-
2,6-Nonadien-1-ol
3-methyl-5-propyl-cyclohexen-1-one
Butanoic acid, 2-methyl-, 3-hexenyl ester, (Z)-
Acetaldehyde, [(3,7-dimethyl-6-octenyl)oxy]-
Lauronitrile
2,4-dimethyl-3-cyclohexene-1-carbaldehyde
2-Buten-1-one, 1-(2,6,6-trimethyl-1,3-cyclohexadien-1-yl)-
2-Buten-1-one, 1-(2,6,6-trimethyl-2-cyclohexen-1-yl)-, (E)-
gamma-Decalactone
trans-4-decenal
decanal
2-Pentylcyclopentanone
1-(2,6,6 Trimethyl 3 Cyclohexen-1-yl)-2 Buten-1-one)
2,6-dimethylheptan-2-ol
Benzene, 1,1'-oxybis-
4-Penten-1-one, 1-(5,5-dimethyl-1-cyclohexen-1-yl)-
Butanoic acid, 2-methyl-, ethyl ester
Ethyl anthranilate
2-Oxabicyclo[2.2.2]octane, 1,3,3-trimethyl-
Eugenol
3-(3-isopropylphenyl)butanal
methyl 2-octynoate
4-(2,6,6-trimethyl-1-cyclohexen-1-yl)-3-buten-2-one
Pyrazine, 2-methoxy-3-(2-methylpropyl)-
Quinoline, 6-secondary buty
Isoeugenol
2H-Pyran-2-one, tetrahydro-6-(3-pentenyl)-

TABLE 1-continued

HIA Perfume Ingredients of Class 1
HIA Ingredient of Class 1

Cis-3-Hexenyl Methyl Carbonate
Linalool
1,6,10-Dodecatriene, 7,11-dimethyl-3-methylene-, (E)-
2,6-dimethyl-5-heptenal
4,7 Methanoindan 1-carboxaldehyde, hexahydro
2-methylundecanal
methyl 2-nonynonate
1,1-dimethoxy-2,2,5-trimethyl-4-hexene
Benzoic acid, 2-hydroxy-, methyl ester
4-Penten-1-one, 1-(5,5-dimethyl-1-Cyclohexen-1-yl)
2H-Pyran, 3,6-dihydro-4 methyl-2-(2-methyl-1-propenyl)-
2,6-Octadienenitrile, 3,7-dimethyl-, (Z)-
2,6-nonadienal
6-Nonenal, (Z)-
nonanal
octanal
2-Nonenenitrile
Acetic acid, 4-methylphenyl ester
Gamma Undecalactone
2-norpinene-2-propionaldehyde 6,6 dimethyl
4-nonanolide
9-decen-1-ol
2H-Pyran, tetrahydro-methyl-2-(2-methyl-1-propenyl)-
5-methyl-3-heptanone oxime
Octanal, 3,7-dimethyl
4-methyl-3-decen-5-ol
10-Undecen-1-al
Pyridine, 2-(1-ethylpropyl)-
Spiro[furan-2(3H),5'-[4,7]methano[5H]indene], decahydro-
Anisic Aldehyde
Flor Acetate
Rose Oxide
Cis 3 Hexenyl Salicylate
Methyl Octin Carbonate
Ethyl-2-Methyl Butyrate Of course, the perfume composition of the invention may comprises one or more HIA perfume ingredient of Class 1.

The first class of HIA perfume ingredient is very effusive and very noticeable when the product is in use as well as on fabric items that come in contact with the wash solution, in particular on synthetic fabrics. Of the perfume ingredients in a given perfume composition, at least 10%, preferably at least 20% and most preferably at least 30% are HIA perfume ingredients of Class 1.

B-High Impact Accord ("HIA") Perfume Ingredients of Class 2

For this second class of perfume ingredients, each Class 2 HIA perfume ingredient of this invention has a B.P., determined at the normal, standard pressure of about 760 mm Hg, of greater than 275° C., an octanol/water partition coefficient P of at least 4,000, and an ODT of less than or equal to 50 parts per billion (ppb). Since the partition coefficients of the preferred perfume ingredients of this invention have high values, they are more conveniently given in the form of their logarithm to the base 10, logP. Thus the preferred perfume ingredients of this invention have ClogP of at least 4.

Table 2 gives some non-limiting examples of HIA perfume ingredients of Class 2.

TABLE 2

HIA Perfume Ingredients of Class 2
HIA Ingredient of Class 2

Naphtho(2,1-B)-furan, 3A-Ethyl Dodecahydro-6,6.9A-Trimethyl
2-(Cyclododecyl)-propan-1-ol
Oxacycloheptadecan-2-one
Ketone.Methyl-2,6.10-Trimethyl-2,5,9-Cyclododecatriene-1-yl
8alpha, 12-oxido-13,14,15,16-tetranorlabdane
Cyclohexane Propanol 2.2,6 Trimethyl-Alpha, Propyl
6,7-Dihydro-1.1,2,3.3-Pentamethyl-4(5H)-Indanone
8-Cyclohexadecen-1-one
2-(2-(4Methyl-3-cyclohexen-1-yl)propyl)-cyclopentanone
Oxacyclohexadecen-2-one
3-Methyl-4(5)-Cyclopentadecenone
3-Methyl-5-(2,2,3-trimethyl-3-cyclopenten-1-yl)-4-penten-2-ol
2,4-Dimethyl-2-(1.1,44,-tetramethyl)tetralin-6-yl)-1,3-dioxolane
Tridecene-2-nitrile
7,Acetyl,1,2,3,4,5,6,7,8-Octahydro-1,1,6,7-Tetra Methyl
Naphthalene
5-Cyclohexadecenone-1

Of course, the perfume composition of the invention may comprises one or more HIA perfume ingredient of Class 2.

The second class of HIA perfume ingredient is very effusive and very noticeable when the product is in use as well as on dried fabric items that have been in contact with the wash solution, in particular on cotton fabrics. Of the perfume ingredients in a given perfume composition, at least 30%, preferably at least 40% and most preferably at least 50% are HIA perfume ingredients of Class 2.

The perfume composition may also comprises some optional conventional to perfume composition materials such as other perfume ingredients not falling within either Class 1 or Class 2, or odourless solvents or oxidation inhibitors, or mixture thereof.

The laundry and cleaning compositions herein comprise from about 0.01% to 50% of the above described HIA perfume composition according to the invention. More preferably, the laundry and cleaning compositions herein comprise from about 0.05% to 8.0% by weight of the HIA perfume composition, even more preferably from about 0.05% to 3.0%, and most preferably from about 0.05% to 1.0% of the HIA perfume composition.

Encapsulating Material

In a preferred embodiment of the invention, the perfume composition is encapsulated.

A wide variety of capsules exist which will allow for delivery of perfume effect at various times in the cleaning or conditioning process.

Examples of such capsules with different encapsulated materials are capsules provided by microencapsulation. One method comprises a capsule core which is coated completely with a material which may be polymeric. U.S. Pat. No. 4,145,184, Brain et al, issued Mar. 20, 1979, and U.S. Pat. No. 4,234,627, Schilling, issued Nov. 18, 1980, teach using a tough coating material which essentialy prohibits the diffusions out of the perfume. The perfume is delivered to fabric via the microcapsules and is then released by rupture of the micropcapsules such as would occur with manipulation of the fabric.

Another method involves providing protection of perfume through the wash cycle and release of perfume in the heat-elevated conditions of the dryer. U.S. Pat. No. 4,096, 072, Brock et al, issued Jun. 20, 1978, teaches a method for delivering fabric conditioning agents to textiles through the wash and dry cycle via particles containing hydrogenated caster oil and a fatty quaternary ammonium salt. Perfume may be incorporated into these particles.

U.S. Pat. No. 4,152,272, Young, teaches incorporating perfume into wax particles to protect the perfume through storage in dry compositions and enhance the deposition of the particles on the fabrics during the rinse by the concommitant use of a cationic surfactant. The perfume then diffuses through the wax matrix of the particles on the fabric in the heat-elevated conditions of the dryer.

In general, the encapsulating materials of the perfumed particles can be a water-insoluable or water-soluble encapsulating material, preferably is a water-soluble encapsulating material.

Nonlimiting examples of useful water-insoluble materials include polyethylenes, polyamides, polystyrenes, polyisoprenes, polycarbonates, polyesters, polyacrylates, vinyl polymers and polyurethanes and mixtures thereof.

Suitable water soluble encapsulating materials are capsules which consist of a matrix of polysaccharide and polyhydroxy compounds such as described in GB 1,464,616. Still other suitable water soluble or water dispersible encapsulating materials comprise dextrins derived from ungelatinized starch acid-esters of substituted dicarboxylic acids such as described in U.S. Pat. No. 3,455,838. These acid-ester dextrins are preferably prepared from such starches as waxy maize, waxy sorghum, sage, tapioca and potato.

When starch is employed, the starches suitable for encapsulating the perfume oils of the present invention can be made from, raw starch, pregelatinized starch, modified starch derived from tubers, legumes, cereal and grains, for example corn starch, wheat starch, rice starch, waxy corn starch, oat starch, cassava starch, waxy barley, waxy rice starch, sweet rice starch, amioca, potato starch, tapioca starch, oat starch, cassava starch, and mixtures thereof.

Modified starches suitable for use as the encapsulating matrix in the present invention include, hydrolyzed starch, acid thinned starch, starch esters of long chain hydrocarbons, starch acetates, starch octenyl succinate, and mixtures thereof.

The term "hydrolyzed starch" refers to oligosaccharide-type materials that are typically obtained by acid and/or enzymatic hydrolysis of starches, preferably corn starch. Suitable hydrolyzed starches for inclusion in the present invention include maltodextrins and corn syrup solids. The hydrolyzed starches for inclusion with the mixture of starch esters have a Dextrose Equivalent (DE) values of from about 10 to about 36 DE. The DE value is a measure of the reducing equivalence of the hydrolyzed starch referenced to dextrose and expressed as a percent (on a dry basis). The higher the DE value, the more reducing sugars present. A method for determining DE values can be found in Standard Analytical Methods of the Member Companies of Corn Industries Research Foundation, 6th ed. Corn Refineries Association, Inc. Washington, D.C. 1980, D-52.

Starch esters having a degree of substitution in the range of from about 0.01% to about 10.0% may be used to encapsulate the perfume oils of the present invention. The hydrocarbon part of the modifying ester should be from a $C_5$ to $C_{16}$ carbon chain. Preferably, octenylsuccinate (OSAN) substituted waxy corn starches of various types such as 1) waxy starch: acid thinned and OSAN substituted, 2) blend of corn syrup solids: waxy starch, OSAN substituted, and dextrinized, 3) waxy starch: OSAN substituted and dextrinized, 4) blend of corn syrup solids or maltodextrins with waxy starch: acid thinned OSAN substituted, and then cooked and spray dried, 5) waxy starch: acid thinned and OSAN substituted then cooked and spray dried, and 6) the high and low viscosities of the above modifications (based on the level of acid treatment) can also be used in the present invention.

Modified starches having emulsifying and emulsion stabilizing capacity such as starch octenyl succinates have the ability to entrap the perfume oil droplets in the emulsion due to the hydrophobic character of the starch modifying agent. The perfume oils remain trapped in the modified starch until dissolved in the wash solution, due to thermodynamic factors i.e., hydrophobic interactions and stabilization of the emulsion because of steric hindrance.

More preferably, the perfume composition of the invention is encapsulated with a water soluble, modified starch to form the modified starch encapsulate. Preferably, the encapsulating material is water-soluble modified starch solid matrix, preferably a starch raw material that has been modified by treating said starch raw material with octenyl-succinic acid anhydride. More preferably the said modified starch is mixed with a polyhydroxy compound before treatment with octenyl-succinic acid anhydride.

Most preferably, for the purpose of the invention the modified starch is a waxy, maize starch, pregelatinised, dextrinised is mixed with sorbitol or any other alcohol type and then treated with octenyl succinic anhydride.

Suitable examples of said encapsulating materials are N-Lok®, manufactured by National Starch, Narlex® (ST and ST2), and Capsul E®. These encapsulating materials comprise pregelatinised waxy maize starch and optionally, glucose. The starch is modified by adding monofunctional substituted groups such as octenyl succinic acid anhydride.

Manufacture of Modified Starch Encapsulated Perfume Composition

The following is a non-limiting example of a suitable process for manufacture of a modified starch encapsulated perfume composition for use in laundry and cleaning compositions according to the present invention.

1. 225 g of CAPSUL modified starch (National Starch & Chemical) is added to 450 g of water at 24° C.
2. The mixture is agitated at 600 RPM (turbine impeller 2 inches in diameter) for 20 minutes.
3. 75 g perfume composition is added near the vortex of the starch solution.
4. The emulsion formed is agitated for an additional 20 minutes (at 600 RPM).
5. Upon achieving a perfume droplet size of less than 15 microns, the emulsion is pumped to a spray drying tower and atomized through a spinning disk with co-current airflow for drying. The inlet air temperature is set at 205–210° C., the exit air temperature is stabilized at 98–103° C.
6. Dried particles of the starch encapsulated perfume composition are collected at the dryer outlet.

Analysis of the finished HIA perfume particle (all % based on weight):

| | |
|---|---|
| Total Perfume Oil | 24.56% |
| Encapsulated Oil | 24.46% |
| Free/Surface Oil | 0.10% |
| Starch | 72.57% |
| Moisture | 2.87% |
| Particle Size Distribution | |
| <50 micrometers | 16% |
| 50–500 micrometers | 83% |
| >500 micrometers | 1% |

Still another preferred manufacture of modified starch encapsulated perfume composition is described in GB 1,464,616, which comprises a mixture of polysaccharide material which is a modified starch and a polyhydroxy compound present in an amount of at least 20% of the mixture by weight and selected from alcohols such as sorbitol, plant-type sugars, lactones, monoethers and acetals. The process comprises forming a solution of the modified starch and the polyhydroxycompound, in proportions such that their mixture softens at the temperature of spray-drying, in water, emulsifying the oil in solution and spray drying said emulsion to remove water therefrom.

Still another process of encapsulation suitable for use herein is described in EP-A-0550,067, and WO 94/19448.

Other known methods of manufacturing the starch encapsulates of the present invention, include but are not limited to, fluid bed agglomeration, extrusion, cooling/crystallization methods and the use of phase transfer catalysts to promote interfacial polymerization. The encapsulated perfume particles can be made by mixing the perfume with the encapsulating matrix, spray-drying emulsions containing the encapsulating material and the perfume. In addition, the particle size of the product from the spray-drying tower can be modified. These modifications can comprise specific processing steps such as post-tower agglomeration steps (e.g. fluidised bed) for enlarging the particle size and/or processing steps wherein the surface properties of the encapsulates are modified, e.g. dusting with hydrophobic silica in order to reduce the hygroscopicity of the encapsulates.

When a laundry and cleaning composition containing the encapsulated perfume composition described herein is added to water the modified starch of the perfume composition begins to dissolve in the water. Not wishing to be bound by theory it is believed that the dissolving modified starch swells and an emulsion of perfume droplets, modified starch and water is formed, the modified starch being the emulsifier and emulsion stabilizer. After the emulsion is formed, the perfume composition begins to coalesce into larger droplets of perfume, which can migrate to either the surface of the solution or to the surface of fabrics in the wash solution due to the relative density difference between the perfume droplets (mostly low density hydrophobic oils) and the wash water. When the droplets reach either interface, they spread out quickly along the surface or interface. The spreading of the perfume droplet at the wash surface increases the surface area from which the perfume composition can volatilize, thereby releasing larger amounts of the perfume into the headspace above the wash solution. This provides a surprisingly strong and consumer noticeable scent in the headspace above the wash solution. Furthermore, the interaction of the perfume droplets with wet fabrics in solution provides a surprisingly strong and consumer noticeable scent on wet and dry fabrics.

Encapsulation of the perfume composition with a modified starch as described above allows for loading of larger amounts of perfume composition than if they were encapsulated in a native starch granule. Encapsulation of perfume composition using cylodextrin is limited by the particle size of the guest molecule (perfume) and the cavity of the host (cyclodextrin). It is difficult to load more than about 20% perfume into a cyclodextrin particle. However, encapsulation with a starch that has been modified to have emulsion properties does not impose this limitation. Since the encapsulation in the present invention is achieved by entrapping perfume oil droplets of less than 15 microns, preferably less than 5 microns and most preferably less than 2.5 microns in size, within the modified starch matrix, while the matrix is being formed by removal of water from the emulsion, more perfume can be loaded based on the type, method and level of modification of the starch. In contrast, traditional cyclodextrin molecules trap the perfume composition completely inside their cavity thereby limiting the size and amount of the perfume oil encapsulated. Loads much greater than 20% are possible when encapsulating with the modified starches described by this invention.

Encapsulation of the volatile perfume composition also minimizes depletion during storage and when the product container is opened. Further, HIA perfumes are generally only released when laundry and cleaning products containing the encapsulated particle are dissolved in the wash solution. Furthermore, the water soluble encapsulating matrix protects the perfume composition from chemical degradation caused in the neat product as well as in the wash solution, by the different surfactant systems or bleaches which are commonly present in the particulate detergent compositions of this invention.

Other suitable matrix materials and process details are disclosed in, e.g., U.S. Pat. No. 3,971,852, Brenner et al., issued Jul. 27, 1976, which is incorporated herein by reference.

Water soluble perfume microcapsules containing conventional, non-HIA perfume oils may optionally be added. This will provide for a further aesthetically pleasing fragrance. These can be obtained commercially, e.g., as IN-CAP® from Polak's Frutal Works, Inc., Middletown, N.Y.; and as Optilok System® encapsulated perfumes from Encapsulated Technology, Inc., Nyack, N.Y.

When the HIA perfume composition is present in encapsulated form, the laundry and cleaning compositions herein preferably comprise from about 0.05% to 8.0% by weight of the encapsulated HIA perfume particle, even more preferably from about 0.05% to 3.0%, and most preferably from about 0.05% to 1.0% of the encapsulated HIA perfume particle. The encapsulated perfume particles preferably have size of from about 1 micron to about 1000 microns, more preferably from about 50 microns to about 500 microns.

Of course, mixtures of perfume composition and encapsulated HIA perfume composition can be employed in the laundry and cleaning composition of the invention. This will allow a desirable immediate release of fragrance upon opening of the package containing the HIA perfume composition and as the product is added to water as well as a long lasting fragrance release on the dry fabric as provided by the encapsulated HIA perfume composition.

According to another aspect of the invention, the perfume composition and/or encapsulated perfume particles are used in laundry and cleaning compositions.

Laundry and Cleaning Compositions

The present invention include both laundry and cleaning compositions which are typically used for laundering fabrics and cleaning hard surfaces such as dishware, floors, bathrooms, toilet, kitchen, animal litter and other surfaces in need of a release of perfume scent in both wet and dry conditions. Accordingly, by laundry and cleaning compositions, these are to be understood to include not only detergent compositions which provide fabric cleaning benefits, but also compositions such as hard surface cleaning which provide hard surface cleaning benefit.

Of course, the present invention may also be used where a need for a release on dry surface is needed such in personal care product like shampoo or shower gel.

Typically the laundry and cleaning composition comprises a detersive ingredient such as detersive surfactants and detersive builders and further optional ingredients as described-hereinafter as optional ingredients.

Detersive Ingredients

Non-limiting examples of surfactants useful herein typically at levels from 1% to 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)$ $CH_3$ and $CH_3(CH_2)_y(CHOSO_3^-M^+)$ $CH_2CH_3$ where x and (y+1) are integers of at least 7, preferably at least 9, and M is a water-solubilizing cation, especially sodium, unsaturated sulfates such as oleyl sulfate, the $C_{10}$–$C_{18}$ alkyl alkoxy sulfates ("$AE_xS$"; especially x up to 7 EO ethoxy sulfates), $C_{10}$–$C_{18}$ alkyl alkoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, cationic surfactants and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 92/06154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are listed in standard texts.

Fully formulated laundry and cleaning compositions preferably contain, in addition to the hereinbefore described components, one or more of the following ingredients.

Detersive Builders

Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least 1% builder, preferably from 1% to 80%. Liquid formulations typically comprise from 5% to 50%, more typically 5% to 30%, by weight, of detergent builder. Granular formulations typically comprise from 1% to 80%, more typically from 5% to 50% by weight, of the detergent builder. Lower or higher levels of builder, however, are not meant to be excluded.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2$:$Na_2O$ ratio in the range 1.0:1 to 3.2:1 and layered silicates, such as the layered sodium silicates described in U.S. Pat. No. 4,664,839. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in DE-A-3, 417,649 and DE-A-3,742,043. SKS-6 is a highly preferred layered silicate for use herein, but other such layered silicates, such as those having the general formula $NaMSi_xO_{2x+1} \cdot yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS-11, as the alpha, beta and gamma forms. As noted above, the delta-$Na_2SiO_5$ (NaSKS-6 form) is most preferred for use herein. Other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates as disclosed in DE 2,321,001.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

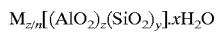

$$M_{z/n}[(AlO_2)_z(SiO_2)_y] \cdot xH_2O$$

wherein z and y are integers usually of at least 6, the molar ratio of z to y is in the range from 1.0 to 0, and x is an integer from 0 to 264, and M is a Group IA or IIA element, e.g., Na, K, Mg, Ca with valence n.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669. Preferred synthetic crystalline aluminosilicate ion exchange materials useful herein are available under the designations Zeolite A, Zeolite P (B), Zeolite MAP and Zeolite X. In an especially preferred embodiment, the crystalline aluminosilicate ion exchange material has the formula:

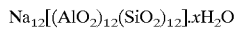

$$Na_{12}[(AlO_2)_{12}(SiO_2)_{12}] \cdot xH_2O$$

wherein x is from 20 to 30, especially 27. This material is known as Zeolite A. Dehydrated zeolites (x=0–10) may also be used herein. Preferably, the aluminosilicate has a particle size of 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. Nos. 3,128,287, 3,635,830. See also "TMS/TDS" builders of U.S. Pat. No. 4,663,071. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, pyromellitic, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Also suitable in the detergent compositions of the present invention are the 3,3-dicarboxy-4-oxa-1,6-hexanedioates and the related compounds disclosed in U.S. Pat. No. 4,566,984. Useful succinic acid builders include the $C_5$–$C_{20}$ alkyl and alkenyl succinic acids and salts thereof. A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in EP 0,200,263.

Other suitable polycarboxylates are disclosed in U.S. Pat. No. 4,144,226 and in U.S. Pat. No. 3,308,067. See also U.S. Pat. No. 3,723,322.

Fatty acids, e.g., $C_{12}$–$C_{18}$ monocarboxylic acids such as oleic acid and/or its salts, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Bleaching Compounds—Bleaching Agents and Bleach Activators

The detergent compositions herein may optionally contain a bleaching system such as bleaching agents or bleaching compositions containing a bleaching agent and one or more bleach activators. When present, bleaching agents will typically be at levels of from 1% to 30%, more typically from 5% to 20%, of the detergent composition, especially for fabric laundering. If present, the amount of bleach activators will typically be from 0.1% to 60%, more typically from 0.5% to 40% of the bleaching composition comprising the bleaching agent-plus-bleach activator.

The bleaching agents used herein can be any of the bleaching agents useful for detergent compositions in textile cleaning or other cleaning purposes that are now known or become known. These include oxygen bleaches as well as other bleaching agents. Perborate bleaches, e.g., sodium perborate (e.g., mono- or tetra-hydrate) can be used herein.

Another category of bleaching agent that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxydodecanedioic acid. Such bleaching agents are disclosed in U.S Pat. Nos. 4,483,781, 740,446, EP 0,133,354, and U.S. Pat. No. 4,412,934. Highly preferred bleaching agents also include 6-nonylamino-6-oxoperoxycaproic acid as described in U.S. Pat. No. 4,634,551.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE, manufactured commercially by DuPont) can also be used.

A preferred percarbonate bleach comprises dry particles having an average particle size in the range from 500 micrometers to 1,000 micrometers, not more than 10% by weight of said particles being smaller than 200 micrometers and not more than 10% by weight of said particles being larger than 1,250 micrometers. Optionally, the percarbonate can be coated with silicate, borate or water-soluble surfactants. Percarbonate is available from various commercial sources such as FMC, Solvay and Tokai Denka.

Mixtures of bleaching agents can also be used.

Peroxygen bleaching agents, the perborates, the percarbonates, etc., are preferably combined with bleach activators, which lead to the in situ production in aqueous solution (i.e., during the washing process) of the peroxy acid corresponding to the bleach activator. Various non-limiting examples of activators are disclosed in U.S. Pat. Nos. 4,915,854, and 4,412,934. The nonanoyloxybenzene sulfonate (NOBS), 3,5,5-tri-methyl hexanoyl oxybenzene sulfonate (ISONOBS) and tetraacetyl ethylene diamine (TAED) activators are typical, and mixtures thereof can also be used. See also U.S. Pat. No. 4,634,551 for other typical bleaches and activators useful herein.

Highly preferred amido-derived bleach activators are those of the formulae:

wherein $R^1$ is an alkyl group containing from 6 to 12 carbon atoms, $R^2$ is an alkylene containing from 1 to 6 carbon atoms, $R^5$ is H or alkyl, aryl, or alkaryl containing from 1 to 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl)oxybenzenesulfonate, (6-nonanamidocaproyl)oxybenzene sulfonate, (6-decanamido-caproyl)oxybenzenesulfonate, and mixtures thereof as described in U.S. Pat. No. 4,634,551, incorporated herein by reference.

Another class of bleach activators comprises the benzoxazin-type activators disclosed by Hodge et al in U.S. Pat. No. 4,966,723. A highly preferred activator of the benzoxazin-type is:

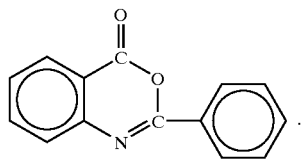

Still another class of preferred bleach activators includes the acyl lactam activators, especially acyl caprolactams and acyl valerolactams of the formulae:

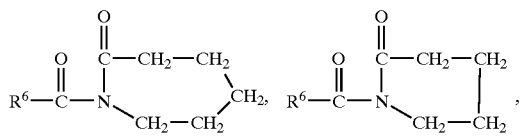

wherein $R^6$ is H or an alkyl, aryl, alkoxyaryl, or alkaryl group containing from 1 to 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. See U.S. Pat. No. 4,033,718. If used, detergent compositions will typically contain from 0.025% to 1.25%, by weight, of such bleaches, especially sulfonate zinc phthalocyanine.

If desired, the bleaching compounds can be catalyzed by means of a manganese compound. Such compounds are well-known in the art and include, for example, the manganese-based catalysts disclosed in U.S. Pat. Nos. 5,246,621, 5,244,594; 5,194,416; 5,114,606; and EP 549,271A1, 549,272A1, 544,440A2, and 544,490A1; Preferred examples of these catalysts include $Mn^{IV}{}_2(u\text{-}O)_3(1,4,7\text{-trimethyl-}1,4,7\text{-triazacyclononane})_2(PF_6)_2$, $Mn^{III}{}_2(u\text{-}O)_1(u\text{-}OAc)_2(1,4,7\text{-trimethyl-}1,4,7\text{-triazacyclononane})_2(ClO_4)_2$, $Mn^{IV}{}_4(u\text{-}O)_6(1,4,7\text{-triazacyclononane})_4(ClO_4)_4$, $Mn^{III}Mn^{IV}{}_4(u\text{-}O)_1(u\text{-}OAc)_2(1,4,7\text{-trimethyl-}1,4,7\text{-triazacyclononane})_2(ClO_4)_3$, $Mn^{IV}(1,4,7\text{-trimethyl-}1,4,7\text{-triazacyclononane})\text{-}(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following U.S. Pat. Nos. 4,728,455; 5,284,944; 5,246,612; 5,256,779; 5,280,117; 5,274,147; 5,153,161; and 5,227,084.

As a practical matter, and not by way of limitation, the compositions and processes herein can be adjusted to provide on the order of at least one part per ten million of the active bleach catalyst species in the aqueous washing liquor, and will preferably provide from 0.1 ppm to 700 ppm, more preferably from 1 ppm to 500 ppm, of the catalyst species in the laundry liquor.

Brighteners

The compositions herein can also optionally contain from 0.005% to 5% by weight of certain types of hydrophilic optical brighteners which also provide a dye transfer inhibition action. If used, the compositions herein will preferably comprise from 0.001% to 1% by weight of such optical brighteners.

The hydrophilic optical brighteners useful in the present invention are those having the structural formula:

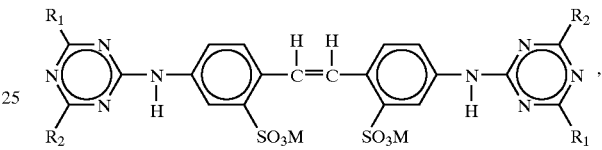

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4'-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX® by Ciba-Geigy Corporation. Tinopal-UNPA-GX is the preferred hydrophilic optical brightener useful in the rinse added compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX® by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX® by Ciba Geigy Corporation.

Soil Release Agent

In the present invention, an optional soil release agent can be added. Typical levels of incorporation in the composition are from 0% to 10%, preferably from 0.2% to 5%, of a soil release agent. Preferably, such a soil release agent is a polymer.

Soil Release agents are desirably used in fabric softening compositions of the instant invention. Any polymeric soil release agent known to those skilled in the art can optionally be employed in the compositions of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

If utilized, soil release agents will generally comprise from about 0.01% to about 10.0%, by weight, of the detergent compositions herein, typically from about 0.1% to about 5%, preferably from about 0.2% to about 3.0%.

The following, all included herein by reference, describe soil release polymers suitable for use in the present invention. U.S. Pat. No. 3,959,230 Hays, issued May 25, 1976; U.S. Pat. No. 3,893,929 Basadur, issued Jul. 8, 1975; U.S. Pat. No. 4,000,093, Nicol, et al., issued Dec. 28, 1976; U.S. Pat. No. 4,702,857 Gosselink, issued Oct. 27, 1987; U.S. Pat. No. 4,968,451, Scheibel et al., issued November 6; U.S. Pat. No. 4,702,857, Gosselink, issued Oct. 27, 1987; U.S. Pat. No. 4,711,730, Gosselink et al., issued Dec. 8, 1987; U.S. Pat. No. 4,721,580, Gosselink, issued Jan. 26, 1988; U.S. Pat. No. 4,877,896, Maldonado et al., issued Oct. 31, 1989; U.S. Pat. No. 4,956,447, Gosselink et al., issued Sep. 11, 1990; U.S. Pat. No. 5,415,807 Gosselink et al., issued May 16, 1995; European Pat. Application 0 219 048, published Apr. 22, 1987 by Kud, et al.

Further suitable soil release agents are described in U.S. Pat. No. 4,201,824, Violland et al.; U.S. Pat. No. 4,240,918 Lagasse et al.; U.S. Pat. No. 4,525,524 Tung et al.; U.S. Pat. No. 4,579,681, Ruppert et al.; U.S. Pat. Nos. 4,240,918; 4,787,989; 4,525,524; EP 279,134 A, 1988, to Rhone-Poulenc Chemie; EP 457,205 A to BASF (1991); and DE 2,335,044 to Unilever N. V., 1974 all incorporated herein by reference.

Commercially available soil release agents include the METOLOSE SM100, METOLOSE SM200 manufactured by Shin-etsu Kagaku Kogyo K. K., SOKALAN type of material, e.g., SOKALAN HP-22, available from BASF (Germany), ZELCON 5126 (from Dupont) and MILEASE T (from ICI).

Scum Dispersant

In the present invention, the premix can be combined with an optional scum dispersant, other than the soil release agent, and heated to a temperature at or above the melting point(s) of the components.

The preferred scum dispersants herein are formed by highly ethoxylating hydrophobic materials. The hydrophobic material can be a fatty alcohol, fatty acid, fatty amine, fatty acid amide, amine oxide, quaternary ammonium compound, or the hydrophobic moieties used to form soil release polymers. The preferred scum dispersants are highly ethoxylated, e.g., more than 17, preferably more than 25, more preferably more than 40, moles of ethylene oxide per molecule on the average, with the polyethylene oxide portion being from 76% to 97%, preferably from 81% to 94%, of the total molecular weight.

The level of scum dispersant is sufficient to keep the scum at an acceptable, preferably unnoticeable to the consumer, level under the conditions of use, but not enough to adversely affect softening. For some purposes it is desirable that the scum is nonexistent. Depending on the amount of anionic or nonionic detergent, etc., used in the wash cycle of a typical laundering process, the efficiency of the rinsing steps prior to the introduction of the compositions herein, and the water hardness, the amount of anionic or nonionic detergent surfactant and detergency builder (especially phosphates and zeolites) entrapped in the fabric (laundry) will vary. Normally, the minimum amount of scum dispersant should be used to avoid adversely affecting softening properties. Typically scum dispersion requires at least 2%, preferably at least 4% (at least 6% and preferably at least 10% for maximum scum avoidance) based upon the level of softener active. However, at levels of 10% (relative to the softener material) or more, one risks loss of softening efficacy of the product especially when the fabrics contain high proportions of nonionic surfactant which has been absorbed during the washing operation.

Preferred scum dispersants are: Brij 700®; Varonic U-250®; Genapol T-500®, Genapol T-800®; Plurafac A-79®; and Neodol 25–50®.

Bactericides

Examples of bactericides used in the compositions of this invention include glutaraldehyde, formaldehyde, 2-bromo-2-nitro-propane-1,3-diol sold by Inolex Chemicals, located in Philadelphia, Pa., under the trade name Bronopol®, and a mixture of 5-chloro-2-methyl-4-isothiazoline-3-one and 2-methyl-4-isothiazoline-3-one sold by Rohm and Haas Company under the trade name Kathon 1 to 1,000 ppm by weight of the agent.

Perfume

The laundry and cleaning composition of the present invention can also contain another perfume composition. Suitable perfumes are disclosed in U.S. Pat. No. 5,500,138, said patent being incorporated herein by reference.

As used herein, perfume includes fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds.

Examples of perfume ingredients useful in the perfume compositions include, but are not limited to, hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-isopropylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma.

Additional examples of fragrance materials include, but are not limited to, orange oil; lemon oil; grapefruit oil; bergamot oil; clove oil; dodecalactone gamma; methyl-2-(2-pentyl-3-oxo-cyclopentyl) acetate; beta-naphthol methyl-ether; methyl-beta-naphthylketone; coumarin; decylaldehyde; benzaldehyde; 4-tert-butylcyclohexyl acetate; alpha, alpha-dimethylphenethyl acetate; methylphenylcarbinyl acetate; Schiff's base of 4-(4-hydroxy-4-methylpentyl)-3-cyclohexene-1-carboxaldehyde and methyl anthranilate; cyclic ethyleneglycol diester of tridecandioic acid; 3,7-dimethyl-2,6-octadiene-1-nitrile; ionone gamma methyl; ionone alpha; ionone beta; petitgrain; methyl cedrylone;

7-acetyl-1,2,3,4,5,6,7,8-octahydro-1,1,6,7-tetramethyl-naphthalene; ionone methyl; methyl- 1,6,10-trimethyl-2,5,9-cyclododecatrien-1-yl ketone; 7-acetyl-1,1,3,4,4,6-hexamethyl tetralin; 4-acetyl-6-tert-butyl-1,1-dimethyl indane; benzophenone; 6-acetyl-1,1,2,3,3,5-hexamethyl indane; 5-acetyl-3-isopropyl-1,1,2,6-tetramethyl indane; 1-dodecanal; 7-hydroxy-3,7-dimethyl octanal; 10-undecen-1-al; iso-hexenyl cyclohexyl carboxaldehyde; formyl tricyclodecan; cyclopentadecanolide; 16-hydroxy-9-hexadecenoic acid lactone; 1,3,4,6,7,8-hexahydro-4,6,6,7,8, 8-hexamethylcyclopenta-gamma-2-benzopyrane; ambroxane; dodecahydro-3a,6,6,9a-tetramethyinaphtho-[2,1b]furan; cedrol; 5-(2,2,3-trimethylcyclopent-3-enyl)-3-methylpentan-2-ol; 2-ethyl-4-(2,2,3-trimethyl-3-cyclopenten-1-yl)-2-buten-1-ol; caryophyllene alcohol; cedryl acetate; para-tert-butylcyclohexyl acetate; patchouli; olibanum resinoid; labdanum; vetivert; copaiba balsam; fir balsam; and condensation products of: hydroxycitronellal and methyl anthranilate; hydroxycitronellal and indol; phenyl acetaldehyde and indol; 4-(4-hydroxy-4-methyl pentyl)-3-cyclohexene-1-carboxaldehyde and methyl anthranilate.

More examples of perfume components are geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl -cyclopentanone; n-decanal; n-dodecanal; 9-decenol-1; phenoxyethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; iso-longifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; ethylene brassylate.

The perfumes useful in the present invention compositions are substantially free of halogenated materials and nitromusks.

Suitable solvents, diluents or carriers for perfumes ingredients mentioned above are for examples, ethanol, isopropanol, diethylene glycol, monoethyl ether, dipropylene glycol, diethyl phthalate, triethyl citrate, etc. The amount of such solvents, diluents or carriers incorporated in the perfumes is preferably kept to the minimum needed to provide a homogeneous perfume solution.

Perfume can be present at a level of from 0% to 10%, preferably from 0.1% to 5%, and more preferably from 0.2% to 3%, by weight of the finished composition. Fabric softener compositions of the present invention provide improved fabric perfume deposition.

Chelating Agents

The compositions and processes herein can optionally employ one or more copper and/or nickel chelating agents ("chelators"). Such water-soluble chelating agents can be selected from the group consisting of amino carboxylates, amino phosphonates, polyfunctionally-substituted aromatic chelating agents and mixtures thereof, all as hereinafter defined. The whiteness and/or brightness of fabrics are substantially improved or restored by such chelating agents and the stability of the materials in the compositions are improved. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetra-aminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder useful with, for example, insoluble builders such as zeolites, layered silicates and the like.

Preferred chelating agents include DETMP, DETPA, NTA, EDDS and mixtures thereof.

If utilized, these chelating agents will generally comprise from about 0.1% to about 15% by weight of the fabric care compositions herein. More preferably, if utilized, the chelating agents will comprise from about 0.1% to about 3.0% by weight of such compositions.

Crystal Growth Inhibitor Component

The compositions of the present invention can further contain a crystal growth inhibitor component, preferably an organodiphosphonic acid component, and/or organo monophosphonic acid, incorporated preferably at a level of from 0.01% to 5%, more preferably from 0.1% to 2% by weight of the compositions.

By organo diphosphonic acid it is meant herein an organo diphosphonic acid which does not contain nitrogen as part of its chemical structure. This definition therefore excludes the organo aminophosphonates, which however may be included in compositions of the invention as heavy metal ion sequestrant components.

The organo diphosphonic acid is preferably a $C_1$–$C_4$ diphosphonic acid, more preferably a $C_2$ diphosphonic acid, such as ethylene diphosphonic acid, or most preferably ethane 1-hydroxy-1,1-diphosphonic acid (HEDP) and may be present in partially or fully ionized form, particularly as a salt or complex.

Still useful herein as crystal growth inhibitor are the organic monophosphonic acid Organo monophosphonic acid or one of its salts or complexes is also suitable for use herein as a CGI.

By organo monophosphonic acid it is meant herein an organo monophosphonic acid which does not contain nitrogen as part of its chemical structure. This definition therefore excludes the organo aminophosphonates, which however may be included in compositions of the invention as heavy metal ion sequestrants.

The organo monophosphonic acid component may be present in its acid form or in the form of one of its salts or complexes with a suitable counter cation. Preferably any salts/complexes are water soluble, with the alkali metal and alkaline earth metal salts/complexes being especially preferred.

A prefered organo monophosphonic acid is 2-phosphonobutane-1,2,4-tricarboxylic acid commercially available from Bayer under the tradename of Bayhibit.

Enzyme

The compositions and processes herein can optionally employ one or more enzymes such as lipases, proteases, cellulase, amylases and peroxidases. A preferred enzyme for use herein is a cellulase enzyme. Indeed, this type of enzyme will further provide a color care benefit to the treated fabric. Cellulases usable herein include both bacterial and fungal types, preferably having a pH optimum between 5 and 9.5. U.S. Pat. No. 4,435,307 discloses suitable fungal cellulases from *Humicola insolens* or *Humicola strain* DSM1800 or a cellulase 212-producing fungus belonging to the genus *Aeromonas,* and cellulase extracted from the hepatopancreas of a marine mollusk, *Dolabella Auricula Solander.* Suitable cellulases are also disclosed in GB-A-2.075.028; GB-A-2.095.275 and DE-OS-2.247.832. CAREZYME® and CELLUZYME® (Novo) are especially useful. Other suitable cellulases are also disclosed in WO 91/17243 to Novo, WO 96/34092, WO 96134945 and EP-A-0,739,982. In practical terms for current commercial preparations, typical amounts are up to 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. In the particular cases where activity of the enzyme preparation can be defined otherwise such as with cellulases, corresponding activity units are preferred (e.g. CEVU or cellulase Equivalent Viscosity Units). For instance, the compositions of the present invention can contain cellulase enzymes at a level equivalent to an activity from 0.5 to 1000 CEVU/gram of composition. Cellulase enzyme preparations used for the purpose of formulating the compositions of this invention typically have an activity comprised between 1,000 and 10,000 CEVU/gram in liquid form, around 1,000 CEVU/gram in solid form.

Optionally, the detergent ingredients can include one or more other detersive adjuncts or other materials for assisting or enhancing cleaning performance, treatment of the substrate to be cleaned, or to modify the aesthetics of the detergent composition.

Other preferred optional ingredients when used are employed at their conventional art-established levels of use, generally from 0% to about 80% by weight of the detergent ingredients, preferably from about 0.5% to about 20% and can include color speckles, suds boosters, suds suppressors, antitarnish and/or anticorrosion agents, soil-suspending agents, dyes, fillers, germicides, alkalinity sources, hydrotropes, antioxidants, enzyme stabilizing agents, solvents, solubilizing agents, clay soil removal antiredeposition agents, polymeric dispersing agents, processing aids, fabric softening components such as clay, static control agents, bleach stabilizers, materials effective for inhibiting the transfer of dyes from one fabric to another during the cleaning process (i.e., dye transfer inhibiting agents), polymeric dispersing agents, optical brighteners or other brightening or whitening agents, other active ingredients, carriers, processing aids, dyes or pigments, solvents for liquid formulations and solid fillers for bar compositions. etc.

Preferably, for the purpose of the invention, the laundry and cleaning composition is selected from a detergent composition, a hard surface cleaning composition, a dishwashing composition, more preferably is a detergent composition, more preferably a granular detergent composition.

Granular Detergent Composition

The perfume composition and encapsulated particles hereinbefore described can be used in both low density (below 550 grams/liter) and high density granular detergent compositions in which the density of the granule is at least 550 grams/liter or in a laundry detergent additive product. Such high density detergent compositions typically comprise from about 30% to about 90% of detersive surfactant.

Low density compositions can be prepared by standard spray-drying processes. Various means and equipment are available to prepare high density granular detergent compositions. Current commercial practice in the field employs spray-drying towers to manufacture granular laundry detergents which often have a density less than about 500 g/l. Accordingly, if spray drying is used as part of the overall process, the resulting spray-dried detergent particles must be further densified using the means and equipment described hereinafter. In the alternative, the formulator can eliminate spray-drying by using mixing, densifying and granulating equipment that is commercially available.

High speed mixer/densifiers can be used in the present process. For example, the device marketed under the trademark "Lodige CB30" Recycler comprises a static cylindrical mixing drum having a central rotating shaft with mixing/cutting blades mounted thereon. Other such apparatus includes the devices marketed under the trademark "Shugi Granulator" and under the trademark "Drais K-TTP 80". Equipment such as that marketed under the trademark "Lodige KM600 Mixer" can be used for further densification.

In one mode of operation, the compositions are prepared and densified by passage through two mixer and densifier machines operating in sequence. Thus, the desired compositional ingredients can be admixed and passed through a Lodige mixture using residence times of 0.1 to 1.0 minute then passed through a second Lodige mixer using residence times of 1 minute to 5 minutes.

In another mode, an aqueous slurry comprising the desired formulation ingredients is sprayed into a fluidized bed of particulate surfactants. The resulting particles can be further densified by passage through a Lodige apparatus, as noted above. The perfume delivery particles are admixed with the detergent composition in the Lodige apparatus.

The final density of the particles herein can be measured by a variety of simple techniques, which typically involve dispensing a quantity of the granular detergent into a container of known volume, measuring the weight of detergent and reporting the density in grams/liter.

Once the low or high density granular detergent "base" composition is prepared, the encapsulated perfume particles of this invention are added thereto by any suitable dry-mixing operation.

Other Applications of the Perfume and/or Encapsulated Perfume Particles of the Invention The perfume composition and/or encapsulated perfume particle hereinbefore described as components of the laundry detergent compositions herein may also be used to impart surprising odor benefits, especially on dry fabrics in the absence of the detersive ingredient of the laundry and cleaning composition embodiments of this invention. Thus, for example, a fabric conditioning composition comprising only the perfume composition and/or encapsulated perfume particle themselves, or comprising an aqueous solution of the perfume composition and/or encapsulated perfume particle, may be added during the rinse cycle of a conventional home laundering operation in order to impart the desired pleasing scent benefits hereinbefore described.

Deposition of Perfume onto Fabric Surfaces

The method of washing fabrics and depositing perfume thereto comprises contacting said fabrics with an aqueous wash liquor comprising at least about 100 ppm of conventional detersive ingredients described hereinabove, as well as at least about 0.1 ppm of the above-disclosed perfume composition and/or encapsulated perfume particles. Preferably, the aqueous liquor comprises from about 500 ppm to about 20,000 ppm of the conventional detersive ingredients and from about 10 ppm to about 200 ppm of the perfume composition and/or encapsulated perfume particles of the invention.

When the perfume composition of the invention is in encapsulated form, the encapsulated perfume particles work under all wash conditions, but they are particularly useful for providing odor benefits to the wet laundry solution during use and on dried fabrics during their storage.

Method of Use

Also provided herein is a method of delivering perfume residuality on surfaces, preferably mixed type of surfaces, which comprises the steps of contacting the surface to be treated with a perfume composition of the invention or composition containing said perfume composition, preferably in an aqueous medium.

By "surface", it is meant any surface onto which the perfume composition can deposit. Typical examples of such material are fabrics, hard surfaces such as dishware, floors, bathrooms, toilet, kitchen and other surfaces in need of a release of a perfume scent such as that with litter like animal litter.

By "mixed type of surfaces", it is meant surfaces made of more than one materials. For examples, where the surface to be treated is a fabric, the fabric or fabric load is composed for example of synthetic and cotton. When the surface is a hard surface, it can be made of plastic and ceramic.

When not specified, by "perfume composition of the invention", it is meant a perfume composition per se, and/or an encapsulated perfume particles, and/or laundry and cleaning composition comprising said perfume composition per se, and/or an encapsulated perfume particles.

EXAMPLES

The following are non-limiting examples of suitable perfume compositions according to the present invention:

| HIA Perfume Ingredient Name | Conc. Wt. % | ODT | Boiling Point ° C. | ClogP |
|---|---|---|---|---|
| Example 1 | | | | |
| 6,7Dihydro-1,1,2,3,3-Penta-Methyl-4(5H)-Indanone | 5 | <50 PPB | 282 | 4.0 |
| Oxacyclohexadecen-2-one | 15 | <50 PPB | 280 | 6.1 |
| Linalool | 25 | <50 PPB | 197 | 3.0 |
| 3-Methyl-5-(2,2,3,trimethyl-3-cyclopenten-1-yl)-4-penten-2-ol | 5 | <50 PPB | 292 | 4.2 |
| Anisic Aldehyde | 10 | <50 PPB | 249 | 2.0 |
| Flor Acetate | 10 | <50 PPB | 265 | 2.4 |
| Ionone Beta | 10 | <50 PPB | 285 | 3.8 |
| Rose Oxide | 10 | <50 PPB | 201 | 2.9 |
| Cyclohexane Propanol 2,2,6 Trimethyl-Alpha-Propyl. | 5 | <50 PPB | 285 | 5.4 |
| 2-(2-(4 methyl-3-Cyclohexen-1-yl)propyl)-cyctopentanone. | 5 | <50 PPB | 301 | 4.4 |
| Total | 100 | | | |
| Example 2 | | | | |
| Cyclal C | 8 | <50 PPB | 199 | 2.4 |
| Naphtho(2.1-B)-furan,3A-Ethyl Dodecahydro-6,6,9A-Trimethyl | 2 | <50 PPB | 316 | 5.3 |
| Rose Oxide | 10 | <50 PPB | 201 | 2.9 |
| Ionone Beta | 25 | <50 PPB | 265 | 3.8 |
| Cis-3-Hexenyl Salicylate | 15 | <50 PPB | 271 | 4.84 |
| Methyl Octine Carbonate | 5 | <50 PPB | 219 | 3.1 |
| 7,Acetyl,1,2,3,4,5,6,7,8-Octahydro-1,1,6,7-Tetra Methyl Naphthalene | 30 | <50 PPB | 304 | 5.4 |
| 3-Methyl-4(5)-Cyclopentadecenone | 2 | <50 PPB | 277 | 5.6 |
| 2-(Cyclododecyl)-propan-1-ol | 3 | <50 PPB | 310 | 5.6 |
| Total | 100 | | | |
| Example 3 | | | | |
| 2-(2-(4 methyl-3-Cyclohexen-1-yl)propyl)-cyclopentanone | 5 | <50 PPB | 301 | 4.4 |
| 6,7-Dihydro-1,1,2,3,3-Pentamethyl-4(5H)-Indanone | 10 | <50 PPB | 282 | 4.0 |
| Ionone Beta | 25 | <50 PPB | 265 | 3.8 |
| Frutene | 15 | <50 PPB | 275 | 2.9 |
| Anisic Aldehyde | 10 | <50 PPB | 249 | 2.0 |
| Ethyl-2-methyl Butyrate | 5 | <50 PPB | 129 | 2.1 |
| 2,4,Dimethyl-2-(1,1,4,4 tetramethyl) tetralin-6-yl)-13-dioxolane | 25 | <50 PPB | 376 | 6.4 |
| 5-Cyclohexadecenone-1 | 3 | <50 PPB | 312 | 6.0 |
| Tridecene-2-nitrile | 2 | <50 PPB | 277 | 5.6 |
| Total | 100 | | | |

The perfume compositions above defined were encapsulated as per the method defined hereinbefore under the title "Manufacture of modified starch Encapsulated Perfume composition"

Abbreviations Used in the Following Laundry and Cleaning Composition Examples

In the laundry and cleaning compositions, the abbreviated component identifications have the following meanings:

In the detergent compositions, the abbreviated component identifications have the following meanings:

LAS: Sodium linear $C_{11-13}$ alkyl benzene sulfonate
TAS: Sodium tallow alkyl sulfate
CxyAS: Sodium $C_{1x}$–$C_{1y}$ alkyl sulfate
C46SAS: Sodium $C_{14}$–$C_{16}$ secondary (2,3)alkyl sulfate
CxyEzS: Sodium $C_{1x}$–$C_{1y}$ alkyl sulfate condensed with z moles of ethylene oxide
CxyEz: $C_{1x}$–$C_{1y}$ predominantly linear primary alcohol condensed with an average of z moles of ethylene oxide
QAS: $R_2.N^+(CH_3)_2(C_2H_4OH)$ with $R_2=C_{12}$–$C_{14}$
QAS 1: $R_2.N^+(CH_3)_2(C_2H_4OH)$ with $R_2=C_8$–$C_{11}$
APA: $C_8$–$C_{10}$ amido propyl dimethyl amine
Soap: Sodium linear alkyl carboxylate derived from an 80/20 mixture of tallow and coconut fatty acids
STS: Sodium toluene sulphonate
CFAA: $C_{12}$–$C_{14}$ (coco) alkyl N-methyl glucamide
TFAA: $C_{16}$–$C_{18}$ alkyl N-methyl glucamide
TPKFA: $C_{12}C_{14}$ topped whole cut fatty acids
STPP: Anhydrous sodium tripolyphosphate
TSPP: Tetrasodium pyrophosphate
Zeolite A: Hydrated sodium aluminosilicate of formula $Na_{12}(AlO_2SiO_2)_{12}.27H_2O$ having a primary particle size in the range from 0.1 to 10 micrometers (weight expressed on an anhydrous basis)
NaSKS-6: Crystalline layered silicate of formula $\delta$-$Na_2Si_2O_5$
Citric acid: Anhydrous citric acid
Borate: Sodium borate
Carbonate: Anhydrous sodium carbonate with a particle size between 200 $\mu$m and 900 $\mu$m
Bicarbonate: Anhydrous sodium bicarbonate with a particle size distribution between 400 $\mu$m and 1200 $\mu$m
Silicate: Amorphous sodium silicate ($SiO_2$:$Na_2O$=2.0:1)
Sulfate: Anhydrous sodium sulfate
Mg sulfate: Anhydrous magnesium sulfate
Citrate: Tri-sodium citrate dihydrate of activity 86.4% with a particle size distribution between 425 $\mu$m and 850 $\mu$m
MA/AA: Copolymer of 1:4 maleic/acrylic acid, average molecular weight about 70,000
MA/AA (1): Copolymer of 4:6 maleic/acrylic acid, average molecular weight about 10,000
AA: Sodium polyacrylate polymer of average molecular weight 4,500
CMC: Sodium carboxymethyl cellulose
Cellulose ether: Methyl cellulose ether with a degree of polymerization of 650 available from Shin Etsu Chemicals
Protease: Proteolytic enzyme, having 3.3% by weight of active enzyme, sold by NOVO Industries A/S under the tradename Savinase
Protease I: Proteolytic enzyme, having 4% by weight of active enzyme, as described in WO 95/10591, sold by Genencor Int. Inc.
Alcalase: Proteolytic enzyme, having 5.3% by weight of active enzyme, sold by NOVO Industries A/S
Cellulase: Cellulytic enzyme, having 0.23% by weight of active enzyme, sold by NOVO Industries A/S under the tradename Carezyme
Amylase: Amylolytic enzyme, having 1.6% by weight of active enzyme, sold by NOVO Industries A/S under the tradename Termamyl 120T
Lipase: Lipolytic enzyme, having 2.0% by weight of active enzyme, sold by NOVO Industries A/S under the tradename Lipolase
Lipase (1): Lipolytic enzyme, having 2.0% by weight of active enzyme, sold by NOVO Industries A/S under the tradename Lipolase Ultra
Endolase: Endoglucanase enzyme, having 1.5% by weight of active enzyme, sold by NOVO Industries A/S
PB4: Sodium perborate tetrahydrate of nominal formula $NaBO_2.3H_2O.H_2O_2$
PB1: Anhydrous sodium perborate bleach of nominal formula $NaBO_2.H_2O_2$
Percarbonate: Sodium percarbonate of nominal formula $2Na_2CO_3.3H_2O_2$
NOBS: Nonanoyloxybenzene sulfonate in the form of the sodium salt
NAC-OBS: (6-nonamidocaproyl)oxybenzene sulfonate
TAED: Tetraacetylethylenediamine
DTPA: Diethylene triamine pentaacetic acid
DTPMP: Diethylene triamine penta (methylene phosphonate), marketed by Monsanto under the Tradename Dequest 2060
EDDS: Ethylenediamine-N,N'-disuccinic acid, (S,S) isomer in the form of its sodium salt.
Photoactivated: Sulfonated zinc phthlocyanine encapsulated in
bleach (1) dextrin soluble polymer
Photoactivated: Sulfonated alumino phthlocyanine encapsulated in
bleach (2) dextrin soluble polymer
Brightener 1: Disodium 4,4'-bis(2-sulphostyryl)biphenyl
Brightener 2: Disodium 4,4'-bis(4-anilino-6-morpholino-1,3,5-triazin-2-yl)amino)stilbene-2:2'-disulfonate
HEDP: 1,1-hydroxyethane diphosphonic acid
PEGx: Polyethylene glycol, with a molecular weight of x (typically 4,000)
PEO: Polyethylene oxide, with an average molecular weight of 50,000
TEPAE: Tetraethylenepentaamine ethoxylate
PVI: Polyvinyl imidosole, with an average molecular weight of 20,000
PVP: Polyvinylpyrolidone polymer, with an average molecular weight of 60,000
PVNO: Polyvinylpyridine N-oxide polymer, with an average molecular weight of 50,000
PVPVI: Copolymer of polyvinylpyrolidone and vinylimidazole, with an average molecular weight of 20,000
QEA: $bis((C_2H_5O)(C_2H_4O)_n)(CH_3)$—$N^+$—$C_6H_{12}$—$N^+$—$(CH_3)$ $bis((C_2H_5O)$—$(C_2H_4O))_n$, wherein n=from 20 to 30
SRP 1: Anionically end capped poly esters
SRP 2: Diethoxylated poly (1, 2 propylene terephtalate) short block polymer
PEI: Polyethyleneimine with an average molecular weight of 1800 and an average ethoxylation degree of 7 ethyleneoxy residues per nitrogen
Silicone antifoam: Polydimethylsiloxane foam controller with siloxane-oxyalkylene copolymer as dispersing agent with a ratio of said foam controller to said dispersing agent of 10:1 to 100:1
Opacifier: Water based monostyrene latex mixture, sold by BASF Aktiengesellschaft under the tradename Lytron 621
Wax: Paraffin wax DEQA: Di-(tallow-oxy-ethyl)dimethyl ammonium chloride.
DEQA (2): Di-(soft-tallowyloxyethyl)hydroxyethyl methyl ammonium methylsulfate.
DTDMAMS: Ditallow dimethyl ammonium methylsulfate.
SDASA: 1:2 ratio of stearyldimethyl amine:triple-pressed stearic acid.
PA30: Polyacrylic acid of average molecular weight of between about 4,500–8,000.
480N: Random copolymer of 7:3 acrylate/methacrylate, average molecular weight about 3,500.
Polygel/carbopol: High molecular weight crosslinked polyacrylates.
Metasilicate: Sodium metasilicate ($SiO_2$:$Na_2O$ ratio=1.0).
Nonionic: $C_{13}$–$C_{15}$ mixed ethoxylated/propoxylated fatty alcohol with an average degree of ethoxylation of 3.8 and an average degree of propoxylation of 4.5.
Neodol 45–13: C14–C15 linear primary alcohol ethoxylate, sold by Shell Chemical CO.
MnTACN: Manganese 1,4,7-trimethyl-1,4,7-triazacyclononane.
PAAC: Pentaamine acetate cobalt(III) salt.
Paraffin: Paraffin oil sold under the tradename Winog 70 by Wintershall.
NaBz: Sodium benzoate.
BzP: Benzoyl Peroxide.
SCS: Sodium cumene sulphonate.
BTA: Benzotriazole.
pH: Measured as a 1% solution in distilled water at 20° C.
HIA 1 Starch encapsulated HIA Perfume particle from Perfume composition Example 1(59%active)
HIA 2 Starch encapsulated HIA Perfume particle from Perfume composition Example 2(59%active)
HIA 3 Starch encapsulated HIA Perfume particle from Perfume composition Example 3(59%active)

In the following formulation examples all levels are quoted as % by weight of the composition unless otherwise stated, and incorporation of the perfume composition in the fully formulated composition is carried out by spray-on unless otherwise mentioned by encapsulation as defined hereinafter by (cap). When encapsulated, the incorporation is made as dry-additive. For HIA, the amount that is specified is the amount of perfume that is delivered by the perfume composition or encapsulated perfume composition.

Example 1

The following high density granular laundry detergent compositions A to F were prepared in accord with the invention:

|  | A | B | C | D | E | F |
|---|---|---|---|---|---|---|
| LAS | 8.0 | 8.0 | 8.0 | 2.0 | 6.0 | 6.0 |
| TAS | — | 0.5 | — | 0.5 | 1.0 | 0.1 |
| C46(S)AS | 2.0 | 2.5 | — | — | — | — |
| C25AS | — | — | — | 7.0 | 4.5 | 5.5 |
| C68AS | 2.0 | 5.0 | 7.0 | — | — | — |
| C25E5 | — | — | 3.4 | 10.0 | 4.6 | 4.6 |
| C25E7 | 3.4 | 3.4 | 1.0 | — | — | — |
| C25E3S | — | — | — | 2.0 | 5.0 | 4.5 |
| QAS | — | 0.8 | — | — | — | — |
| QAS (I) | — | — | — | 0.8 | 0.5 | 1.0 |
| Zeolite A | 18.1 | 18.0 | 14.1 | 18.1 | 20.0 | 18.1 |

-continued

|  | A | B | C | D | E | F |
|---|---|---|---|---|---|---|
| Citric acid | — | — | — | 2.5 | — | 2.5 |
| Carbonate | 13.0 | 13.0 | 27.0 | 10.0 | 10.0 | 13.0 |
| SKS-6 | — | — | — | 10.0 | — | 10.0 |
| Silicate | 1.4 | 1.4 | 3.0 | 0.3 | 0.5 | 0.3 |
| Citrate | — | 1.0 | — | 3.0 | — | — |
| Sulfate | 26.1 | 26.1 | 26.1 | 6.0 | — | — |
| Mg sulfate | 0.3 | — | — | 0.2 | — | 0.2 |
| MA/AA | 0.3 | 0.3 | 0.3 | 4.0 | 1.0 | 1.0 |
| CMC | 0.2 | 0.2 | 0.2 | 0.2 | 0.4 | 0.4 |
| PB4 | 9.0 | 9.0 | 5.0 | — | — | — |
| Percarbonate | — | — | — | — | 18.0 | 18.0 |
| TAED | 1.5 | 0.4 | 1.5 | — | 3.9 | 4.2 |
| NAC-OBS | — | 2.0 | 1.0 | — | — | — |
| DTPMP | 0.25 | 0.25 | 0.25 | 0.25 | — | — |
| SRP I | — | — | — | 0.2 | — | 0.2 |
| EDDS | — | 0.25 | 0.4 | — | 0.5 | 0.5 |
| CFAA | — | 1.0 | — | 2.0 | — | — |
| HEDP | 0.3 | 0.3 | 0.3 | 0.3 | 0.4 | 0.4 |
| QEA | — | — | — | 0.2 | — | 0.5 |
| Protease I | — | — | 0.26 | 1.0 | — | — |
| Protease | 0.26 | 0.26 | — | — | 1.5 | 1.0 |
| Cellulase | 0.3 | — | — | 0.3 | 0.3 | 0.3 |
| Amylase | 0.1 | 0.1 | 0.1 | 0.4 | 0.5 | 0.5 |
| Lipase (1) | 0.3 | — | — | 0.5 | 0.5 | 0.5 |
| Photoactivated bleach (ppm) | 15 ppm | 15 ppm | 15 ppm | — | 20 ppm | 20 ppm |
| PVNO/PVPVI | — | — | — | 0.1 | — | — |
| Brightener 1 | 0.09 | 0.09 | 0.09 | — | 0.09 | 0.09 |
| Perfume spray on | 0 | 0.3 | 0.3 | 0.4 | 0.4 | 0.4 |
| HIA 1 | 0.3 | 0.4 (cap) | 0.1 | 0.7 (cap) | 0.6 (cap) | 0.2 (cap) |
| Silicone antifoam | 0.5 | 0.5 | 0.5 | — | 0.3 | 0.3 |
| Misc/minors to 100% |  |  |  |  |  |  |
| Density in g/liter | 850 | 850 | 850 | 550 | 850 | 850 |

Example 2

The following granular laundry detergent compositions G to L of particular utility under European machine wash conditions were prepared in accord with the invention:

|  | G | H | I | J | K | L | M |
|---|---|---|---|---|---|---|---|
| LAS | 5.5 | 7.5 | 7.5 | 5.0 | 5.0 | 6.0 | 7.0 |
| TAS | 1.25 | 1.86 | 1.86 | — | 0.8 | 0.4 | 0.3 |
| C24AS/C25AS | — | 2.24 | 2.24 | 5.0 | 5.0 | 5.0 | 2.2 |
| C25E3S | — | 0.76 | 0.76 | 1.0 | 1.5 | 3.0 | 1.0 |
| C45E7 | 3.25 | — | — | — | — | — | 3.0 |
| TFAA | — | — | — | 2.0 | — | — | — |
| C25E5 | — | 5.5 | 5.5 | — | — | — | — |
| QAS | 0.8 | — | — | — | — | — | — |
| QAS II | — | 0.7 | 0.7 | 1.0 | 0.5 | 1.0 | 0.7 |
| STPP | 19.7 | — | — | — | — | — | — |
| Zeolite A | — | 19.5 | 19.5 | 25.0 | 19.5 | 20.0 | 17.0 |
| NaSKS-6/citric acid (79:21) | — | 10.6 | 10.6 | — | 10.6 | — | — |
| NaSKS-6 | — | — | — | 9.0 | — | 10.0 | 10.0 |
| Carbonate | 6.1 | 21.4 | 21.4 | 9.0 | 10.0 | 10.0 | 18.0 |
| Bicarbonate | — | 2.0 | 2.0 | 7.0 | 5.0 | — | 2.0 |
| Silicate | 6.8 | — | — | — | 0.3 | 0.5 | — |
| Citrate | — | — | — | 4.0 | 4.0 | — | — |
| Sulfate | 39.8 | — | — | — | 5.0 | — | 12.0 |
| Mg sulfate | — | — | — | 0.1 | 0.2 | 0.2 | — |
| MA/AA | 0.5 | 1.6 | 1.6 | 3.0 | 4.0 | 1.0 | 1.0 |
| CMC | 0.2 | 0.4 | 0.4 | 1.0 | 1.0 | 0.4 | 0.4 |

-continued

|  | G | H | I | J | K | L | M |
|---|---|---|---|---|---|---|---|
| PB4 | 5.0 | 12.7 | 12.7 | — | — | — | — |
| Percarbonate | — | — | — | — | — | 18.0 | 15.0 |
| TAED | 0.5 | 3.1 | 3.1 | — | — | 5.0 | — |
| NAC-OBS | 1.0 | 3.5 | 3.5 | — | — | — | 2.5 |
| DTPMP | 0.25 | 0.2 | 0.2 | 0.3 | 0.4 | — | 0.2 |
| HEDP | — | 0.3 | 0.3 | — | 0.3 | 0.3 | 0.3 |
| QEA | — | — | — | 1.0 | 1.0 | 1.0 | — |
| Protease I | — | — | — | — | 0.5 | 1.2 | — |
| Protease | 0.26 | 0.85 | 0.85 | 0.9 | 1.0 | — | 0.7 |
| Lipase (1) | 0.15 | 0.15 | 0.15 | 0.3 | 0.3 | 0.3 | 0.2 |
| Cellulase | 0.28 | 0.28 | 0.28 | 0.2 | 0.2 | 0.3 | 0.3 |
| Amylase | 0.1 | 0.1 | 0.1 | 0.4 | 0.4 | 0.6 | 0.2 |
| PVNO/PVPVI | — | — | — | 0.2 | 0.2 | — | — |
| PVP | 0.9 | 1.3 | 1.3 | — | — | — | 0.9 |
| SRP 1 | — | — | — | 0.2 | 0.2 | 0.2 | — |
| Photo-activated bleach (1) (ppm) | 15 ppm | 27 ppm | 27 ppm | — | — | 20 ppm | 20 ppm |
| Photo-activated bleach (2) (ppm) | 15 ppm | — | — | — | — | — | — |
| Brightener 1 | 0.08 | 0.19 | 0.19 | — | — | 0.09 | 0.15 |
| Brightener 2 | — | 0.04 | 0.04 | — | — | — | — |
| Perfume | 0 | 0.3 | 0.2 | 0.4 | 0.3 | 0.4 | 0.3 |
| HIA 2 | 0.3 | 0.4 | 0.4 (cap) | 0.3 (cap) | 0.7 (cap) | 0.6 (cap) | 0.1 (cap) |
| HIA 2 | — | — | 0.1 | — | — | — | — |
| Silicone antifoam | 0.5 | 2.4 | 2.4 | 0.3 | 0.5 | 0.3 | 2.0 |
| Minors/misc to 100% | | | | | | | |
| Density in g/liter | 750 | 750 | 750 | 750 | 750 | 750 | 750 |

Example 3

The following detergent formulations of particular utility under European machine wash conditions were prepared in accord with the invention.

|  | N | O | P | Q |
|---|---|---|---|---|
| Blown powder | | | | |
| LAS | 6.0 | 5.0 | 11.0 | 6.0 |
| TAS | 2.0 | — | — | 2.0 |
| Zeolite A | 24.0 | — | — | 20.0 |
| STPP | — | 27.0 | 24.0 | — |
| Sulfate | 4.0 | 6.0 | 13.0 | — |
| MA/AA | 1.0 | 4.0 | 6.0 | 2.0 |
| Silicate | 1.0 | 7.0 | 3.0 | 3.0 |
| CMC | 1.0 | 1.0 | 0.5 | 0.6 |
| Brightener 1 | 0.2 | 0.2 | 0.2 | 0.2 |
| Silicone antifoam | 1.0 | 1.0 | 1.0 | 0.3 |
| DTPMP | 0.4 | 0.4 | 0.2 | 0.4 |
| Spray on | | | | |
| Brightener | 0.02 | — | — | 0.02 |
| C45E7 | — | — | — | 5.0 |
| C45E2 | 2.5 | 2.5 | 2.0 | — |
| C45E3 | 2.6 | 2.5 | 2.0 | — |
| Perfume | 0.5 | 0.3 | 0.5 | 0.2 |
| Silicone antifoam | 0.3 | 0.3 | 0.3 | — |
| Dry additives | | | | |
| QEA | — | — | — | 1.0 |
| EDDS | 0.3 | — | — | — |
| Sulfate | 2.0 | 3.0 | 5.0 | 10.0 |
| Carbonate | 6.0 | 13.0 | 15.0 | 14.0 |
| Citric acid | 2.5 | — | — | 2.0 |
| QAS II | 0.5 | — | — | 0.5 |
| SKS-6 | 10.0 | — | — | — |
| Percarbonate | 18.5 | — | — | — |
| PB4 | — | 18.0 | 10.0 | 21.5 |
| TAED | 2.0 | 2.0 | — | 2.0 |
| NAC-OBS | 3.0 | 2.0 | 4.0 | — |
| Protease | 1.0 | 1.0 | 1.0 | 1.0 |
| Lipase | — | 0.4 | — | 0.2 |
| Lipase (1) | 0.4 | — | 0.4 | — |
| Amylase | 0.2 | 0.2 | 0.2 | 0.4 |
| Brightener 1 | 0.05 | — | — | 0.05 |
| HIA 3 | 0.1 | 0.3 | 0.15 (cap) | 0.4 (cap) |
| Misc/minor to 100% | | | | |

Example 4

The following granular detergent formulations were prepared in accord with the invention.

|  | R | S | T | U | V | W |
|---|---|---|---|---|---|---|
| Blown powder | | | | | | |
| LAS | 23.0 | 8.0 | 7.0 | 9.0 | 7.0 | 7.0 |
| TAS | — | — | — | — | 1.0 | — |
| C45AS | 6.0 | 6.0 | 5.0 | 8.0 | — | — |
| C45AES | — | 1.0 | 1.0 | 1.0 | — | — |
| C45E35 | — | — | — | — | 2.0 | 4.0 |
| Zeolite A | 10.0 | 18.0 | 14.0 | 12.0 | 10.0 | 10.0 |
| MA/AA | — | 0.5 | — | — | — | 2.0 |
| MA/AA (1) | 7.0 | — | — | — | — | — |
| AA | — | 3.0 | 3.0 | 2.0 | 3.0 | 3.0 |
| Sulfate | 5.0 | 6.3 | 14.3 | 11.0 | 15.0 | 19.3 |
| Silicate | 10.0 | 1.0 | 1.0 | 1.0 | 1.0 | 1.0 |
| Carbonate | 15.0 | 20.0 | 10.0 | 20.7 | 8.0 | 6.0 |
| PEG 4000 | 0.4 | 1.5 | 1.5 | 1.0 | 1.0 | 1.0 |
| DTPA | — | 0.9 | 0.5 | — | — | 0.5 |
| Brightener 2 | 0.3 | 0.2 | 0.3 | — | 0.1 | 0.3 |
| Spray on | | | | | | |
| C45E7 | — | 2.0 | — | — | 2.0 | 2.0 |
| C25E9 | 3.0 | — | — | — | — | — |
| C23E9 | — | — | 1.5 | 2.0 | — | 2.0 |
| Perfume | 0.3 | 0.3 | 0.3 | 2.0 | 0.3 | 0.3 |
| Agglomerates | | | | | | |
| C45AS | — | 5.0 | 5.0 | 2.0 | — | 5.0 |
| LAS | — | 2.0 | 2.0 | — | — | 2.0 |
| Zeolite A | — | 7.5 | 7.5 | 8.0 | — | 7.5 |
| Carbonate | — | 4.0 | 4.0 | 5.0 | — | 4.0 |
| PEG 4000 | — | 0.5 | 0.5 | — | — | 0.5 |
| Misc (water etc) | — | 2.0 | 2.0 | 2.0 | — | 2.0 |
| Dry additives | | | | | | |
| QAS (I) | — | — | — | — | 1.0 | — |
| Citric acid | — | — | — | — | 2.0 | — |
| PB4 | — | — | — | — | 12.0 | 1.0 |
| PB1 | 4.0 | 1.0 | 3.0 | 2.0 | — | — |
| Percarbonate | — | — | — | — | 2.0 | 10.0 |
| Carbonate | — | 5.3 | 1.8 | — | 4.0 | 4.0 |
| NOBS | 4.0 | — | 6.0 | — | — | 0.6 |
| Methyl cellulose | 0.2 | — | — | — | — | — |
| SKS-6 | 8.0 | — | — | — | — | — |

-continued

|  | R | S | T | U | V | W |
|---|---|---|---|---|---|---|
| STS | — | — | 2.0 | — | 1.0 | — |
| Cumene sulfonic acid | — | 1.0 | — | — | — | 2.0 |
| Lipase | 0.2 | — | 0.2 | — | 0.2 | 0.4 |
| Cellulase | 0.2 | 0.2 | 0.2 | 0.3 | 0.2 | 0.2 |
| Amylase | 0.2 | — | 0.1 | — | 0.2 | — |
| Protease | 0.5 | 0.5 | 0.5 | 0.3 | 0.5 | 0.5 |
| PVPVI | — | — | — | — | 0.5 | 0.1 |
| PVP | — | — | — | — | 0.5 | — |
| PVNO | — | — | 0.5 | 0.3 | — | — |
| QEA | — | — | — | — | 1.0 | — |
| SRP1 | 0.2 | 0.5 | 0.3 | — | 0.2 | — |
| HIA 1 | 0.4 (cap) | 0.1 (cap) | 0.3 (cap) | 0.2 (cap) | 0.3 (cap) | 0.3 (cap) |
| Silicone antifoam | 0.2 | 0.4 | 0.2 | 0.4 | 0.1 | — |
| Mg sulfate | — | — | 0.2 | — | 0.2 | — |
| Misc/minors to 100% | | | | | | |

Example 5

The following nil bleach-containing detergent formulations of particular use in the washing of coloured clothing, according to the present invention were prepared:

|  | X | Y | Z |
|---|---|---|---|
| Blown Powder | | | |
| Zeolite A | 15.0 | 15.0 | — |
| Sulfate | 0.0 | 5.0 | — |
| LAS | 3.0 | 3.0 | — |
| DTPMP | 0.4 | 0.5 | — |
| CMC | 0.4 | 0.4 | — |
| MA/AA | 4.0 | 4.0 | — |
| Agglomerates | | | |
| C45AS | — | — | 11.0 |
| LAS | 6.0 | 5.0 | — |
| TAS | 3.0 | 2.0 | — |
| Silicate | 4.0 | 4.0 | — |
| Zeolite A | 10.0 | 15.0 | 13.0 |
| CMC | — | — | 0.5 |
| MA/AA | — | — | 2.0 |
| Carbonate | 9.0 | 7.0 | 7.0 |
| Spray On | | | |
| Perfume | 0.3 | 0.3 | 0.5 |
| C45E7 | 4.0 | 4.0 | 4.0 |
| C25E3 | 2.0 | 2.0 | 2.0 |
| Dry additives | | | |
| MA/AA | — | — | 3.0 |
| NaSKS-6 | — | — | 12.0 |
| Citrate | 10.0 | — | 8.0 |
| Bicarbonate | 7.0 | 3.0 | 5.0 |
| Carbonate | 8.0 | 5.0 | 7.0 |
| PVPVI/PVNO | 0.5 | 0.5 | 0.5 |
| Alcalase | 0.5 | 0.3 | 0.9 |
| Lipase | 0.4 | 0.4 | 0.4 |
| Amylase | 0.6 | 0.6 | 0.6 |
| Cellulase | 0.6 | 0.6 | 0.6 |
| HIA 1 | 0.1 | 0.3(cap) | 0.3(cap) |
| Silicone antifoam | 5.0 | 5.0 | 5.0 |
| Dry additives | | | |
| Sulfate | 0.0 | 9.0 | 0.0 |
| Misc/minors to 100% | 100.0 | 100.0 | 100.0 |
| Density (g/liter) | 700 | 700 | 700 |

Example 6

The following granular detergent formulations were prepared in accord with the invention.

|  | AA | BB | CC | DD |
|---|---|---|---|---|
| Base granule | | | | |
| Zeolite A | 30.0 | 22.0 | 24.0 | 10.0 |
| Sulfate | 10.0 | 5.0 | 10.0 | 7.0 |
| MA/AA | 3.0 | — | — | — |
| AA | — | 1.6 | 2.0 | — |
| MA/AA (1) | — | 12.0 | — | 6.0 |
| LAS | 14.0 | 10.0 | 9.0 | 20.0 |
| C45AS | 8.0 | 7.0 | 9.0 | 7.0 |
| C45AES | — | 1.0 | 1.0 | — |
| Silicate | — | 1.0 | 0.5 | 10.0 |
| Soap | — | 2.0 | — | — |
| Brightener 1 | 0.2 | 0.2 | 0.2 | 0.2 |
| Carbonate | 6.0 | 9.0 | 10.0 | 10.0 |
| PEG 4000 | — | 1.0 | 1.5 | — |
| DTPA | — | 0.4 | — | — |
| Spray on | | | | |
| C25E9 | — | — | — | 5.0 |
| C45E7 | 1.0 | 1.0 | — | — |
| C23E9 | — | 1.0 | 2.5 | — |
| Perfume | 0.2 | 0.3 | 0.3 | — |
| Dry additives | | | | |
| Carbonate | 5.0 | 10.0 | 18.0 | 8.0 |
| PVPVI/PVNO | 0.5 | — | 0.3 | — |
| Protease | 1.0 | 1.0 | 1.0 | 0.5 |
| Lipase | 0.4 | — | — | 0.4 |
| Amylase | 0.1 | — | — | 0.1 |
| Cellulase | 0.1 | 0.2 | 0.2 | 0.1 |
| NOBS | — | 4.0 | — | 4.5 |
| PB1 | 1.0 | 5.0 | 1.5 | 6.0 |
| Sulfate | 4.0 | 5.0 | — | 5.0 |
| SRP1 | — | 0.4 | — | — |
| HIA 1 | 0.35 (cap) | 0.2 (cap) | 0.1 | 0.4 (cap) |
| Sud supressor | — | 0.5 | 0.5 | — |
| Misc/minor to 100% | | | | |

Example 7

The following granular detergent compositions were prepared in accord with the invention.

|  | EE | FF | GG |
|---|---|---|---|
| Blown powder | | | |
| Zeolite A | 20.0 | — | 15.0 |
| STPP | — | 20.0 | — |
| Sulphate | — | — | 5.0 |
| Carbonate | — | — | 5.0 |
| TAS | — | — | 1.0 |
| LAS | 6.0 | 6.0 | 6.0 |
| C68AS | 2.0 | 2.0 | — |
| Silicate | 3.0 | 8.0 | — |
| MA/AA | 4.0 | 2.0 | 2.0 |
| CMC | 0.6 | 0.6 | 0.2 |
| Brightener 1 | 0.2 | 0.2 | 0.1 |
| DTPMP | 0.4 | 0.4 | 0.1 |
| STS | — | — | 1.0 |
| Spray on | | | |
| C45E7 | 5.0 | 5.0 | 4.0 |
| Silicone antifoam | 0.3 | 0.3 | 0.1 |
| Perfume | 0.2 | 0.2 | 0.3 |
| Dry additives | | | |
| QEA | — | — | 1.0 |
| Carbonate | 14.0 | 9.0 | 10.0 |
| PB1 | 1.5 | 2.0 | — |
| PB4 | 18.5 | 13.0 | 13.0 |

-continued

|  | EE | FF | GG |
|---|---|---|---|
| TAED | 2.0 | 2.0 | 2.0 |
| QAS (I) | — | — | 1.0 |
| Photoactivated bleach | 15 ppm | 15 ppm | 15 ppm |
| SKS-6 | — | — | 3.0 |
| Protease | 1.0 | 1.0 | 0.2 |
| Lipase | 0.2 | 0.2 | 0.2 |
| Amylase | 0.4 | 0.4 | 0.2 |
| Cellulase | 0.1 | 0.1 | 0.2 |
| Sulfate | 10.0 | 20.0 | 5.0 |
| HIA 1 | 0.1 (cap) | 0.1 (cap) | 0.2 (cap) |
| Misc/minors to 100% |  |  |  |
| Density (g/liter) | 700 | 700 | 700 |

Example 8

The following detergent compositions, according to the present invention were prepared:

|  | HH | II | JJ |
|---|---|---|---|
| Blown Powder |  |  |  |
| Zeolite A | 15.0 | 15.0 | 15.0 |
| Sulfate | 0.0 | 5.0 | 0.0 |
| LAS | 3.0 | 3.0 | 3.0 |
| QAS | — | 1.5 | 1.5 |
| DTPMP | 0.4 | 0.2 | 0.4 |
| EDDS | — | 0.4 | 0.2 |
| CMC | 0.4 | 0.4 | 0.4 |
| MA/AA | 4.0 | 2.0 | 2.0 |
| Agglomerates |  |  |  |
| LAS | 5.0 | 5.0 | 5.0 |
| TAS | 2.0 | 2.0 | 1.0 |
| Silicate | 3.0 | 3.0 | 4.0 |
| Zeolite A | 8.0 | 8.0 | 8.0 |
| Carbonate | 8.0 | 8.0 | 4.0 |
| Spray On |  |  |  |
| Perfume | 0.3 | 0.3 | 0.3 |
| C45E7 | 2.0 | 2.0 | 2.0 |
| C25E3 | 2.0 | — | — |
| Dry additives |  |  |  |
| Citrate | 5.0 | — | 2.0 |
| Bicarbonate | — | 3.0 | — |
| Carbonate | 8.0 | 15.0 | 10.0 |
| TAED | 6.0 | 2.0 | 5.0 |
| PB1 | 14.0 | 7.0 | 10.0 |
| PEO | — | — | 0.2 |
| HIA 1 | 0.4 (cap) | 0.2 (cap) | 0.7 (cap) |
| Bentonite clay | — | — | 10.0 |
| Protease | 1.0 | 1.0 | 1.0 |
| Lipase | 0.4 | 0.4 | 0.4 |
| Amylase | 0.6 | 0.6 | 0.6 |
| Cellulase | 0.6 | 0.6 | 0.6 |
| Silicone antifoam | 5.0 | 5.0 | 5.0 |
| Dry additives |  |  |  |
| Sodium sulfate | 0.0 | 3.0 | 0.0 |
| Misc/minors to 100% | 100.0 | 100.0 | 100.0 |
| Density (g/liter) | 850 | 850 | 850 |

Example 9

The following detergent formulations, according to the present invention were prepared:

|  | KK | LL | MM | NN |
|---|---|---|---|---|
| LAS | 18.0 | 14.0 | 24.0 | 20.0 |
| QAS | 0.7 | 1.0 | — | 0.7 |
| TFM | — | 1.0 | — | — |
| C23E56.5 | — | — | 1.0 | — |
| C45E7 | — | 1.0 | — | — |
| C45E3S | 1.0 | 2.5 | 1.0 | — |
| STPP | 32.0 | 18.0 | 30.0 | 22.0 |
| Silicate | 9.0 | 5.0 | 9.0 | 8.0 |
| Carbonate | 11.0 | 7.5 | 10.0 | 5.0 |
| Bicarbonate | — | 7.5 | — | — |
| PB1 | 3.0 | 1.0 | — | — |
| PB4 | — | 1.0 | — | — |
| NOBS | 2.0 | 1.0 | — | — |
| DTPMP | — | 1.0 | — | — |
| DTPA | 0.5 | — | 0.2 | 0.3 |
| SRP 1 | 0.3 | 0.2 | — | 0.1 |
| MA/AA | 1.0 | 1.5 | 2.0 | 0.5 |
| CMC | 0.8 | 0.4 | 0.4 | 0.2 |
| PEI | — | — | 0.4 | — |
| Sodium sulfate | 20.0 | 10.0 | 20.0 | 30.0 |
| Mg sulfate | 0.2 | — | 0.4 | 0.9 |
| Protease | 0.8 | 1.0 | 0.5 | 0.5 |
| Amylase | 0.5 | 0.4 | — | 0.25 |
| Lipase | 0.2 | — | 0.1 | — |
| Cellulase | 0.15 | — | — | 0.05 |
| Photoactivated bleach (ppm) | 30 ppm | 20 ppm | — | 10 ppm |
| HIA 2 | 0.3 (cap) | 0.5 (cap) | 0.1 (cap) | 0.2 (cap) |
| Perfume spray on | 0.3 | 0.3 | 0.1 | 0.2 |
| Brightener 1/2 | 0.0S | 0.2 | 0.08 | 0.1 |
| Misc/minors to 100% |  |  |  |  |

Example 10

The following liquid detergent formulations were prepared in accord with the invention (levels are given as parts per weight).

|  | OO | PP | QQ | RR | SS |
|---|---|---|---|---|---|
| LAS | 11.5 | 8.8 | — | 3.9 | — |
| C25E2.5S | — | 3.0 | 18.0 | — | 16.0 |
| C45E2.25S | 11.5 | 3.0 | — | 15.7 | — |
| C23E9 | — | 2.7 | 1.8 | 2.0 | 1.0 |
| C23E7 | 3.2 | — | — | — | — |
| CFAA | — | — | 5.2 | — | 3.1 |
| TPKFA | 1.6 | — | 2.0 | 0.5 | 2.0 |
| Citric acid (50%) | 6.5 | 1.2 | 2.5 | 4.4 | 2.5 |
| Calcium formate | 0.1 | 0.06 | 0.1 | — | — |
| Sodium formate | 0.5 | 0.06 | 0.1 | 0.05 | 0.05 |
| Sodium cumene sulfonate | 4.0 | 1.0 | 3.0 | 1.18 | — |
| Borate | 0.6 | — | 3.0 | 2.0 | 2.9 |
| Sodium hydroxide | 5.8 | 2.0 | 3.5 | 3.7 | 2.7 |
| Ethanol | 1.75 | 1.0 | 3.6 | 4.2 | 2.9 |
| 1,2 propanediol | 3.3 | 2.0 | 8.0 | 7.9 | 5.3 |
| Monoethanolamine | 3.0 | 1.5 | 1.3 | 2.5 | 0.8 |
| TEPAE | 1.6 | — | 1.3 | 1.2 | 1.2 |
| Protease | 1.0 | 0.3 | 1.0 | 0.5 | 0.7 |
| Lipase | — | — | 0.1 | — | — |
| Cellulase | — | — | 0.1 | 0.2 | 0.05 |
| Amylase | — | — | — | 0.1 | — |
| SRP1 | 0.2 | — | 0.1 | — | — |
| DTPA | — | — | 0.3 | — | — |
| PVNO | — | — | 0.3 | — | 0.2 |
| Perfume | 0.4 | 0.4 | 0.4 | 0.4 | 0.4 |

-continued

| | OO | PP | QQ | RR | SS |
|---|---|---|---|---|---|
| HIA 1 | 0.2 | 0.5 | 0.1 | 0.3 | 0.1 |
| Brightener 1 | 0.2 | 0.07 | 0.1 | — | — |
| Silicone antifoam | 0.04 | 0.02 | 0.1 | 0.1 | 0.1 |
| Water/minors | | | | | |

Example 11

The following liquid detergent formulations were prepared in accord with the invention (levels are given in parts per weight):

| | TT | UU | VV | WW | XX | YY | ZZ | AB |
|---|---|---|---|---|---|---|---|---|
| LAS | 10.0 | 13.0 | 9.0 | — | 25.0 | — | — | — |
| C25AS | 4.0 | 1.0 | 2.0 | 10.0 | — | 13.0 | 18.0 | 15.0 |
| C25E3S | 1.0 | — | — | 3.0 | — | 2.0 | 2.0 | 4.0 |
| C25E7 | 6.0 | 8.0 | 13.0 | 2.5 | — | — | 4.0 | 4.0 |
| TFAA | — | — | — | 4.5 | — | 6.0 | 8.0 | 8.0 |
| APA | — | 1.4 | — | — | 3.0 | 1.0 | 2.0 | — |
| TPKFA | 2.0 | 13.0 | 7.0 | — | 15.0 | 11.0 | 11.0 | — |
| Citric acid | 2.0 | 3.0 | 1.0 | 1.5 | 1.0 | 1.0 | 1.0 | 1.0 |
| Dodecenyl/tetradecenyl succinic acid | 12.0 | 10.0 | — | — | 15.0 | — | — | — |
| Rape seed fatty acid | 4.0 | 2.0 | 1.0 | — | 1.0 | — | 3.5 | — |
| Ethanol | 4.0 | 4.0 | 7.0 | 2.0 | 7.0 | 2.0 | 3.0 | 2.0 |
| 1,2 Propanediol | 4.0 | 4.0 | 2.0. | 7.0 | 6.0 | 8.0 | 10.0 | 13.0 |
| Monoethanol-amine | — | — | — | 5.0 | — | — | 9.0 | 9.0 |
| Triethanol-amine | — | — | 8.0 | — | — | — | — | — |
| TEPAE | 0.5 | — | 0.5 | 0.2 | — | — | 0.4 | 0.3 |
| DTPMP | 1.0 | 1.0 | 0.5 | 1.0 | 2.0 | 1.2 | 1.0 | — |
| Protease | 0.5 | 0.5 | 0.4 | 0.25 | — | 0.5 | 0.3 | 0.6 |
| Alcalase | — | — | — | — | 1.5 | — | — | — |
| Lipase | — | 0.10 | — | 0.01 | — | — | 0.15 | 0.15 |
| Amylase | 0.25 | 0.25 | 0.6 | 0.5 | 0.25 | 0.9 | 0.6 | 0.6 |
| Cellulase | — | — | — | 0.05 | — | — | 0.15 | 0.15 |
| Endolase | — | — | — | 0.10 | — | — | 0.07 | — |
| SRP2 | 0.3 | — | 0.3 | 0.1 | — | — | 0.2 | 0.1 |
| Boric acid | 0.1 | 0.2 | 1.0 | 2.0 | 1.0 | 1.5 | 2.5 | 2.5 |
| Calcium chloride | — | 0.02 | — | 0.01 | — | — | — | — |
| Bentonite clay | — | — | — | — | 4.0 | 4.0 | — | — |
| Brightener 1 | — | 0.4 | — | — | 0.1 | 0.2 | 0.3 | — |
| Sud supressor | 0.1 | 0.3 | — | 0.1 | 0.4 | — | — | — |
| Opacifier | 0.5 | 0.4 | — | 0.3 | 0.8 | 0.7 | — | — |
| Perfume | 0 | 0.2 | 0.2 | 0.4 | 0.4 | 0.4 | 0.4 | 0.4 |
| HIA 1 | 0.4 | 0.2 | 0.1 | 0.3 | 0.1 | 0.5 | 0.4 | 0.5 |
| Water/minors | | | | | | | | |
| NaOH up to pH | 8.0 | 8.0 | 7.6 | 7.7 | 8.0 | 7.5 | 8.0 | 8.2 |

Example 12

The following liquid detergent compositions were prepared in accord with the invention (levels are given in parts per weight).

| | AC | AD |
|---|---|---|
| LAS | 27.6 | 18.9 |
| C45AS | 13.8 | 5.9 |
| C13E8 | 3.0 | 3.1 |
| Oleic acid | 3.4 | 2.5 |
| Citric acid | 5.4 | 5.4 |
| Sodium hydroxide | 0.4 | 3.6 |
| Calcium formate | 0.2 | 0.1 |
| Sodium formate | — | 0.5 |
| Ethanol | 7.0 | — |
| Monoethanolamine | 16.5 | 8.0 |
| 1,2 propanediol | 5.9 | 5.5 |
| Xylene sulfonic acid | — | 2.4 |
| TEPAE | 1.5 | 0.8 |
| Protease | 1.5 | 0.6 |
| PEG | — | 0.7 |
| Brightener 2 | 0.4 | 0.1 |
| Perfume | 0.5 | 0.3 |
| HIA 1 | 0.2 | 0.1 |
| Water/minors | | |

Example 13

The following laundry bar detergent compositions were prepared in accord with the invention (levels are given in parts per weight).

| | AE | AF | AG | AH | AI | AJ | AK | AL |
|---|---|---|---|---|---|---|---|---|
| LAS | — | — | 19.0 | 15.0 | 21.0 | 6.75 | 8.8 | — |
| C28AS | 30.0 | 13.5 | — | — | — | 15.75 | 11.2 | 22.5 |
| Sodium laurate | 2.5 | 9.0 | — | — | — | — | — | — |
| Zeolite A | 2.0 | 1.25 | — | — | — | 1.25 | 1.25 | 1.25 |
| Carbonate | 20.0 | 3.0 | 13.0 | 8.0 | 10.0 | 15.0 | 15.0 | 10.0 |
| Calcium carbonate | 27.5 | 39.0 | 35.0 | — | — | 40.0 | — | 40.0 |
| Sulfate | 5.0 | 5.0 | 3.0 | 5.0 | 3.0 | — | — | 5.0 |
| TSPP | 5.0 | — | — | — | — | 5.0 | 2.5 | — |
| STPP | 5.0 | 15.0 | 10.0 | — | — | 7.0 | 8.0 | 10.0 |
| Bentonite clay | — | 10.0 | — | — | 5.0 | — | — | — |
| DTPMP | — | 0.7 | 0.6 | — | 0.6 | 0.7 | 0.7 | 0.7 |
| CMO | — | 1.0 | 1.0 | 1.0 | 1.0 | — | — | 1.0 |
| Talc | — | — | 10.0 | 15.0 | 10.0 | — | — | — |
| Silicate | — | — | 4.0 | 5.0 | 3.0 | — | — | — |
| PVNO | 0.02 | 0.03 | — | 0.01 | — | 0.02 | — | — |
| MA/AA | 0.4 | 1.0 | — | — | 0.2 | 0.4 | 0.5 | 0.4 |
| SRP1 | 0.3 | 0.3 | 0.3 | 0.3 | 0.3 | 0.3 | 0.3 | 0.3 |
| Protease | — | 0.12 | — | 0.08 | 0.08 | — | — | 0.1 |
| Lipase | — | 0.1 | — | 0.1 | — | — | — | — |
| Amylase | — | — | 0.8 | — | — | — | 0.1 | — |
| Cellulase | — | 0.15 | — | — | 0.15 | 0.1 | — | — |
| PEO | — | 0.2 | — | 0.2 | 0.3 | — | — | 0.3 |
| Perfume | 1.0 | 0.5 | 0.3 | 0.2 | 0.4 | — | — | 0.4 |
| Mg sulfate | — | — | 3.0 | 3.0 | 3.0 | — | — | — |
| HIA 1 | 0.3 | 0.4 | 0.1 | 0.2 | 0.1 | 0.05 | 0.1 | 0.3 |
| | | (cap) | | (cap) | | (cap) | (cap) | (cap) |
| Brightener | 0.15 | 0.10 | 0.15 | — | — | — | — | 0.1 |
| Photoactivated bleach (ppm) | — | 15.0 | 15.0 | 15.0 | 15.0 | — | — | 15.0 |

Example 14

The following fabric softener and dryer added fabric conditioner compositions were prepared according to the present invention:

|  | AM | AN | AO | AP | AQ |
|---|---|---|---|---|---|
| DEQA | 2.6 | 19.0 | — | — | — |
| DEQA(2) | — | — | — | — | 51.8 |
| DTMAMS | — | — | — | 26.0 | — |
| SDASA | — | — | 70.0 | 42.0 | 40.2 |
| Stearic acid of IV = 0 | 0.3 | — | — | — | — |
| Neodol 45-13 | — | — | 13.0 | — | — |
| Hydrochloride acid | 0.02 | 0.02 | — | — | — |
| Ethanol | — | — | 1.0 | — | — |
| HIA 1 | 0.2 | 0.4 | 0.6 | 0.2 | 0.2 |
| Perfume | 1.0 | 1.0 | 0.75 | 1.0 | 1.5 |
| Glycoperse S-20 | — | — | — | — | 15.4 |
| Glycerol monostearate | — | — | — | 26.0 | — |
| Digeranyl Succinate | — | — | 0.38 | — | — |
| Silicone antifoam | 0.01 | 0.01 | — | — | — |
| Electrolyte | — | 0.1 | — | — | — |
| Clay | — | — | — | 3.0 | — |
| Dye | 10 ppm | 25 ppm | 0.01 | — | — |
| Water and minors | 100% | 100% | — | — | — |

Example 15

The following detergent additive compositions were prepared according to the present invention:

|  | AR | AS | AT |
|---|---|---|---|
| LAS | — | 5.0 | 5.0 |
| STPP | 30.0 | — | 20.0 |
| Zeolite A | — | 35.0 | 20.0 |
| PB1 | 20.0 | 15.0 | — |
| TAED | 10.0 | 8.0 | — |
| Perfume | — | 0.3 | 0.4 |
| HIA 1 | 0.3 | 0.5 (cap) | 0.6 (cap) |
| Protease | — | 0.3 | 0.3 |
| Amylase | — | 0.06 | 0.06 |
| Minors, water and miscellaneous | | Up to 100% | |

Example 16

The following compact high density (0.96 Kg/l) dishwashing detergent compositions were prepared according to the present invention:

|  | AU | AV | AW | AX | AY | AZ | BA | BC |
|---|---|---|---|---|---|---|---|---|
| STPP | — | — | 54.3 | 51.4 | 51.4 | — | — | 50.9 |
| Citrate | 35.0 | 17.0 | — | — | — | 46.1 | 40.2 | — |
| Carbonate | — | 17.5 | 14.0 | 14.0 | 14.0 | — | 8.0 | 32.1 |
| Bicarbonate | — | — | — | — | — | 25.4 | — | — |
| Silicate | 32.0 | 14.8 | 14.8 | 10.0 | 10.0 | 1.0 | 25.0 | 3.1 |
| Metasilicate | — | 2.5 | — | 9.0 | 9.0 | — | — | — |
| PB1 | 1.9 | 9.7 | 7.8 | 7.8 | 7.8 | — | — | — |
| PB4 | 8.6 | — | — | — | — | — | — | — |
| Percarbonate | — | — | — | — | — | 6.7 | 11.8 | 4.8 |
| Nonionic | 1.5 | 2.0 | 1.5 | 1.7 | 1.5 | 2.6 | 1.9 | 5.3 |
| TAED | 5.2 | 2.4 | — | — | — | 22 | — | 1.4 |
| HEDP | — | 1.0 | — | — | — | — | — | — |
| DTPMP | — | 0.6 | — | — | — | — | — | — |
| MnTACN | — | — | — | — | — | — | 0.008 | — |
| PAAC | — | — | 0.008 | 0.01 | 0.007 | — | — | — |
| BzP | — | — | — | — | 1.4 | — | — | — |
| Paraffin | 0.5 | 0.5 | 0.5 | 0.5 | 0.5 | 0.6 | — | — |
| Perfume | 0 | 0.1 | 0.2 | 0.2 | 0.2 | 0.3 | 0.3 | 0.4 |
| HIA | 0.5 | 0.3 | 0.3 | 0.4 | 0.5 | 0.5 | 0.6 | 0.6 |
|  | (cap) | (cap) | (cap) | (cap) | (cap) | (cap) | (cap) | (cap) |
| Protease | 0.072 | 0.072 | 0.029 | 0.053 | 0.046 | 0.026 | 0.059 | 0.06 |

-continued

|  | AU | AV | AW | AX | AY | AZ | BA | BC |
|---|---|---|---|---|---|---|---|---|
| Amylase | 0.012 | 0.012 | 0.0de | 0.012 | 0.013 | 0.009 | 0.017 | 0.03 |
| Lipase | — | 0.001 | — | 0.005 | — | — | — | — |
| BTA | 0.3 | 0.3 | 0.3 | 0.3 | 0.3 | — | 0.3 | 0.3 |
| MA/AA | — | — | — | — | — | — | 4.2 | — |
| 480N | 3.3 | 6.0 | — | — | — | — | — | 0.9 |
| Perfume | 0.2 | 0.2 | 0.2 | 0.2 | 0.2 | 0.2 | 0.1 | 0.1 |
| Sulphate | 7.0 | 20.0 | 5.0 | 2.2 | 0.8 | 12.0 | 4.6 | — |
| pH | 10.8 | 11.0 | 10.8 | 11.3 | 11.3 | 9.6 | 10.8 | 10.9 |
| Miscellaneous and water | | | | Up to 100% | | | | |

Example 17

The following granular dishwashing detergent compositions of bulk density 1.02 Kg/L were prepared according to the present invention:

|  | BD | BE | BF | BG | BH | BI | BJ | BK |
|---|---|---|---|---|---|---|---|---|
| STPP | 30.0 | 30.0 | 33.0 | 34.2 | 29.6 | 31.1 | 26.6 | 17.6 |
| Carbonate | 30.5 | 30.5 | 31.0 | 30.0 | 23.0 | 39.4 | 4.2 | 45.0 |
| Silicate | 7.4 | 7.4 | 7.5 | 7.2 | 13.3 | 3.4 | 43.7 | 12.4 |
| Metasilicate | — | — | 4.5 | 5.1 | — | — | — | — |
| Percarbonate | — | — | — | — | — | 4.0 | — | — |
| PB1 | 4.4 | 4.2 | 4.5 | 4.5 | — | — | — | — |
| NADCC | — | — | — | — | 2.0 | — | 1.6 | 1.0 |
| Nonionic | 1.2 | 1.0 | 0.7 | 0.8 | 1.9 | 0.7 | 0.6 | 0.3 |
| TAED | 1.0 | — | — | — | — | 0.8 | — | — |
| PAAC | — | 0.004 | 0.004 | 0.004 | — | — | — | — |
| BZP | — | — | — | 1.4 | — | — | — | — |
| Paraffin | 0.25 | 0.25 | 0.25 | 0.25 | — | — | — | — |
| Perfume | 0 | 0.1 | 0.2 | 0.3 | 0.3 | 0.3 | 0.3 | 0.3 |
| HIA | 0.1 | 0.1 | 0.1 | 0.1 | 0.15 | 0.2 | 0.3 | 0.4 |
|  | | | | (cap) | (cap) | (cap) | (cap) | (cap) |
| Protease | 0.036 | 0.015 | 0.03 | 0.028 | — | 0.03 | — | — |
| Amylase | 0.003 | 0.003 | 0.01 | 0.006 | — | 0.01 | — | — |
| Lipase | 0.005 | — | 0.001 | — | — | — | — | — |
| BTA | 0.15 | 0.15 | 0.15 | 0.15 | — | — | — | — |
| Sulphate | 23.4 | 25.0 | 22.0 | 18.5 | 30.1 | 19.3 | 23.1 | 23.6 |
| pH | 10.8 | 10.8 | 11.3 | 11.3 | 10.7 | 11.5 | 12.7 | 10.9 |
| Miscellaneous and water | | | | Up to 100% | | | | |

Example 18

The following tablet detergent compositions were prepared according to the present invention by compression of a granular dishwashing detergent composition at a pressure of 13 KN/cm² using a standard 12 head rotary press:

|  | BL | BM | BN | BO | BP | BQ |
|---|---|---|---|---|---|---|
| STPP | — | 48.8 | 49.2 | 38.0 | — | 46.8 |
| Citrate | 26.4 | — | — | — | 31.1 | — |
| Carbonate | — | 5.0 | 14.0 | 15.4 | 14.4 | 23.0 |
| Silicate | 26.4 | 14.8 | 15.0 | 12.6 | 17.7 | 2.4 |
| HIA 1 | 0.1 | 0.2 | 0.1 | 0.1 | 0.1 | 0.1 |
|  | | | | (cap) | | |
| Protease | 0.058 | 0.072 | 0.041 | 0.033 | 0.052 | 0.013 |
| Amylase | 0.01 | 0.03 | 0.012 | 0.007 | 0.016 | 0.002 |
| Lipase | 0.005 | — | — | — | — | — |
| PB1 | 1.6 | 7.7 | 12.2 | 10.6 | 15.7 | — |
| PB4 | 6.9 | — | — | — | — | 14.4 |
| Nonionic | 1.5 | 2.0 | 1.5 | 1.65 | 0.8 | 6.3 |
| PAAC | — | — | 0.02 | 0.009 | — | — |
| MnTACN | — | — | — | — | 0.007 | — |

-continued

|  | BL | BM | BN | BO | BP | BQ |
|---|---|---|---|---|---|---|
| TAED | 4.3 | 2.5 | — | — | 1.3 | 1.8 |
| HEDP | 0.7 | — | — | 0.7 | — | 0.4 |
| DTPMP | 0.65 | — | — | — | — | — |
| Paraffin | 0.4 | 0.5 | 0.5 | 0.55 | — | — |
| BTA | 0.2 | 0.3 | 0.3 | 0.3 | — | — |
| PA30 | 3.2 | — | — | — | — | — |
| MA/AA | — | — | — | — | 4.5 | 0.55 |
| Perfume | — | — | 0.05 | 0.05 | 0.2 | 0.2 |
| Sulphate | 24.0 | 13.0 | 2.3 | — | 10.7 | 3.4 |
| Weight of tablet | 25 g | 25 g | 20 g | 30 g | 18 g | 20 g |
| pH | 10.6 | 10.6 | 10.7 | 10.7 | 10.9 | 11.2 |
| Miscellaneous and water | Up to 100% | | | | | |

Example 19

The following liquid dishwashing detergent compositions of density 1.40 Kg/L were prepared according to the present invention:

|  | BR | BS | BT | BU |
|---|---|---|---|---|
| STPP | 17.5 | 17.5 | 17.2 | 16.0 |
| Carbonate | 2.0 | — | 2.4 | — |
| Silicate | 5.3 | 6.1 | 14.6 | 15.7 |
| NaOCl | 1.15 | 1.15 | 1.15 | 1.25 |
| Polygen/carbopol | 1.1 | 1.0 | 1.1 | 1.25 |
| Nonionic | — | — | 0.1 | — |
| Perfume | — | 0.1 | 0.1 | 0.2 |
| NaBz | 0.75 | 0.75 | — | — |
| HIA 2 | 0.1 | 0.1 | 0.2 | 0.2 |
| NaOH | — | 1.9 | — | 3.5 |
| KOH | 2.8 | 3.5 | 3.0 | — |
| pH | 11.0 | 11.7 | 10.9 | 11.0 |
| Sulphate, miscellaneous and water | up to 100% | | | |

Example 20

The following liquid rinse aid compositions were prepared according to the present invention:

|  | BV | BW | BX |
|---|---|---|---|
| Nonionic | 12.0 | — | 14.5 |
| Nonionic blend | — | 64.0 | — |
| Citric | 3.2 | — | 6.5 |
| HEDP | 0.5 | — | — |
| PEG | — | 5.0 | — |
| SCS | 4.8 | — | 7.0 |
| Ethanol | 6.0 | 8.0 | — |
| Perfume | 0 | 0.4 | 0.4 |
| HIA | 0.2 | 0.2 | 0.3 |
| pH of the liquid | 2.0 | 7.5 | / |
| Miscellaneous and water | Up to 100% | | |

Example 21

The following liquid dishwashing compositions were prepared according to the present invention:

|  | BY | BZ | CA | CB | CD |
|---|---|---|---|---|---|
| C17ES | 28.5 | 27.4 | 19.2 | 34.1 | 34.1 |
| Amine oxide | 2.6 | 5.0 | 2.0 | 3.0 | 3.0 |
| C12 glucose amide | — | — | 6.0 | — | — |
| Betaine | 0.9 | — | — | 2.0 | 2.0 |
| Xylene sulfonate | 2.0 | 4.0 | — | 2.0 | — |
| Neodol C11E9 | — | — | 5.0 | — | — |
| Polyhydroxy fatty acid amide | — | — | — | 6.5 | 6.5 |
| Sodium diethylene pentaacetate (40%) | — | — | 0.03 | — | — |
| TAED | — | — | — | 0.06 | 0.06 |
| Sucrose | — | — | — | 1.5 | 1.5 |
| Ethanol | 4.0 | 5.5 | 5.5 | 9.1 | 9.1 |
| Alkyl diphenyl oxide disulfonate | — | — | — | — | 2.3 |
| Ca formate | — | — | — | 0.5 | 1.1 |
| Ammonium citrate | 0.06 | 0.1 | — | — | — |
| Na chloride | — | 1.0 | — | — | — |
| Mg chloride | 3.3 | — | 0.7 | — | — |
| Ca chloride | — | — | 0.4 | — | — |
| Na sulfate | — | — | 0.06 | — | — |
| Mg sulfate | 0.08 | — | — | — | — |
| Mg hydroxide | — | — | — | 2.2 | 2.2 |
| Na hydroxide | — | — | — | 1.1 | 1.1 |
| Hydrogen peroxide | 200 ppm | 0.16 | 0.006 | — | — |
| HIA3 | 0.1 | 0.2 | 0.3 | 0.1 | 0.2 |
| Protease | 0.017 | 0.005 | .0035 | 0.003 | 0.002 |
| Perfume | 0.18 | 0.09 | 0.09 | 0.2 | 0.2 |
| Water and minors | Up to 100% | | | | |

Example 22

The following liquid hard surface cleaning compositions were prepared according to the present invention:

|  | CE | CF | CG | CH | CI |
|---|---|---|---|---|---|
| HIA 1 | 0.3 | 0.3 | 0.5 | 0.3 | 0.3 |
| Amylase | 0.01 | 0.002 | 0.005 | — | — |
| Protease | 0.05 | 0.01 | 0.02 | — | — |
| Hydrogen peroxide | — | — | — | 6.0 | 6.8 |
| Acetyl triethyl citrate | — | — | — | 2.5 | — |
| DTPA | — | — | — | 0.2 | — |
| Butyl hydroxy toluene | — | — | — | 0.05 | — |
| EDTA* | 0.05 | 0.05 | 0.05 | — | — |
| Citric/Citrate | 2.9 | 2.9 | 2.9 | 1.0 | — |
| LAS | 0.5 | 0.5 | 0.5 | — | — |
| C12 AS | 0.5 | 0.5 | 0.5 | — | — |
| C10AS | — | — | — | — | 1.7 |
| C12(E)S | 0.5 | 0.5 | 0.5 | — | — |
| C12,13 E6.5 nonionic | 7.0 | 7.0 | 7.0 | — | — |
| Neodol 23-6.5 | — | — | — | 12.0 | — |
| Dobanol 23-3 | — | — | — | — | 1.5 |
| Dobanol 91-10 | — | — | — | — | 1.6 |
| C25AE1.8S | — | — | — | 6.0 | — |
| Na paraffin sulphonate | — | — | — | 6.0 | — |
| Perfume | — | 1.0 | 1.0 | 0.5 | 0.2 |
| Propanediol | — | — | — | 1.5 | — |
| Ethoxylated tetraethylene pentaimine | — | — | — | 1.0 | — |
| 2, Butyl octanol | — | — | — | — | 0.5 |
| Hexyl carbitol** | 1.0 | 1.0 | 1.0 | — | — |
| SCS | 1.3 | 1.3 | 1.3 | — | — |
| pH adjusted to | 7–12 | 7–12 | 7–12 | 4 | — |
| Miscellaneous and water | Up to 100% | | | | |

*Na4 ethylenediamine diacetic acid
**Diethylene glycol monohexyl ether

Example 23

The following spray composition for cleaning of hard surfaces and removing household mildew was prepared according to the present invention:

|  |  |
|---|---|
| HIA 1 | 0.1 |
| Amylase | 0.01 |
| Protease | 0.01 |
| Na octyl sulfate | 2.0 |
| Na dodecyl sulfate | 4.0 |
| Na hydroxide | 0.8 |
| Silicate | 0.04 |
| Butyl carbitol* | 4.0 |
| Perfume | 0.35 |
| Water/minors | up to 100% |

*Diethylene glycol monobutyl ether

Example 24

The following lavatory cleansing block compositions were prepared according to the present invention.

|  | CK | CL | CM |
|---|---|---|---|
| C16–18 fatty alcohol/50EO | 80.0 | — | — |
| LAS | — | — | 80.0 |
| Nonionic | — | 1.0 | — |
| Oleoamide surfactant | — | 26.0 | — |
| Partially esterified copolymer of vinylmethyl ether and maleic anhydride viscosity 0.1–0.5 | 5.0 | — | — |
| Polyethylene glycol MW 8000 | — | 39.0 | — |
| Water-soluble K-polyacrylate MW 4000–8000 | — | 12.0 | — |
| Water-soluble Na-copolymer of acrylamide (70%) and acryclic acid (30%) low MW | — | 19.0 | — |
| Na triphosphate | 10.0 | — | — |
| Carbonate | — | — | 8.0 |
| HIA 1 | 0.5 | 1.0 | 0.5 (cap) |
| Dye | 2.5 | 1.0 | 1.0 |
| Perfume | 3.0 | — | 7.0 |
| KOH/HCL solution |  | pH 6–11 |  |

Example 25

The following toilet bowl cleaning composition was prepared according to the present invention.

|  | CN | CO |
|---|---|---|
| C14–15 linear alcohol 7EO | 2.0 | 10.0 |
| Citric acid | 10.0 | 5.0 |
| HIA 1 | 1.0 | 2.0 |
| DTPMP | — | 1.0 |
| Dye | 2.0 | 1.0 |
| Perfume | 3.0 | 3.0 |
| NaOH | pH 6–11 |  |
| Water and minors | Up to 100% |  |

Example 26

The following liquid personal cleansing compositions containing soap were prepared according to the present invention:

|  | CP | CQ |
|---|---|---|
| HIA 1 | 0.1 | 0.1 |
| Protease | 0.10 | — |
| Soap (K or Na) | 15.00 | — |

-continued

|  | CP | CQ |
|---|---|---|
| 30% Laurate | — | — |
| 30% Myristate | — | — |
| 25% Palmitate | — | — |
| 15% Stearate | — | — |
| Fatty acids (above ratios) | 4.5 | — |
| Na Lauryl Sarcosinate | 6.0 | — |
| Na Laureth Sulfate | 0.7 | 12.0 |
| Cocamidopropylbetaine | 1.3 | 3.0 |
| Glycerine | 15.0 | — |
| Propylene Glycol | 9.0 | — |
| Ethylene glycol distearate (EDTA) | 1.5 | 0.4 |
| Cocoamide MEA | — | 0.2 |
| Perfume | — | 0.6 |
| *Polyquaterium-7 | — | 0.1 |
| DMDM hydantoin | — | 0.14 |
| Sodium benzoate | — | 0.25 |
| Tetrasodium EDTA dihydrate | — | 0.1 |
| Citric | — | 0.1 |
| Propylparaben | 0.10 | — |
| Methylparaben | 0.20 | — |
| Calcium sulfate | 3.0 | — |
| Acetic acid | 3.0 | — |
| Water and minors | Up to 100% |  |
| KOH/NaOH (pH adjustment) |  |  |

*Copolymer of dimethyl dialkyl ammonium chloride and acrylamide

Example 27

The following personal cleansing bar composition was prepared according to the present invention:

|  |  |
|---|---|
| Na Cocoyl Isethionate | 47.20 |
| Na Cetearyl sulfate | 9.14 |
| Paraffin | 9.05 |
| Na Soap (in situ) | 3.67 |
| Na Isethionate | 5.51 |
| Na Chloride | 0.45 |
| Titanium Dioxide | 0.4 |
| Trisodium EDTA | 0.1 |
| Trisodium Etidronate | 0.1 |
| Perfume | 1.20 |
| Sulfate | 0.87 |
| HIA 1 | 0.5 |
| Protease | 0.10 |
| Miscellaneous and minors | Up to 100% |

Example 28

The following shampoo compositions were prepared according to the present invention:

|  | CS | CT | CU | CV | CW | CX |
|---|---|---|---|---|---|---|
| NH4 laureth-3 sulfate | 16.0 | 18.0 | 10.0 | 16.0 | 14.0 | 18.0 |
| NH4 lauryl sulfate | 5.0 | 6.0 | 3.0 | 3.0 | 4.0 | 6.0 |
| Na lauryl sarcosinate | — | — | 2.0 | — | — | — |
| Cocoamide MEA | 1.0 | — | — | 1.0 | 0.6 | — |
| Dimethicone 40/60 | 0.8 | 1.0 | 0.4 | 3.0 | 2.0 | 1.0 |
| Polyquaternium-10 | — | — | 0.01 | — | 0.2 | — |
| Cetyl alcohol | 0.5 | 0.4 | — | 0.4 | 0.4 | 0.1 |
| Stearyl alcohol | — | 0.2 | — | 0.5 | 0.1 | 0.2 |
| Panthenyl ethyl ether | 0.2 | — | — | 0.2 | 0.2 | 0.2 |
| Panthenol 10% | — | 0.03 | — | 0.03 | — | — |
| Tallow | — | — | — | — | — | 0.5 |
| Mineral oil | — | — | — | — | 0.5 | — |
| Tetrasodium EDTA | 0.09 | 0.09 | 0.07 | 0.09 | 0.09 | 0.09 |
| DMDM Hydantoin | 0.14 | 0.14 | 0.14 | 0.12 | 0.14 | 0.14 |

-continued

|  | CS | CT | CU | CV | CW | CX |
|---|---|---|---|---|---|---|
| Sodium benzoate | 0.25 | 0.25 | — | 0.25 | 0.25 | 0.25 |
| Citrate | 1.0 | — | — | 1.0 | 1.0 | — |
| Citric | 0.1 | — | 0.3 | 0.1 | — | — |
| Na hydroxide | — | — | 0.3 | — | — | — |
| Na phosphate | — | 0.6 | — | — | — | 0.6 |
| Disodium phosphate | — | 0.2 | — | — | — | 0.2 |
| Na chloride | 1.5 | 1.5 | 3.0 | 1.5 | 2.0 | 1.5 |
| PEG-12 | — | — | 0.15 | — | — | 0.4 |
| NH4 xylene sulfonnate | 0.4 | 0.4 | — | 0.4 | 0.4 | 0.4 |
| Ethylene glycol distearate | 1.0 | 3.0 | 1.5 | 2.0 | 3.0 | 0.5 |
| Zinc pyrithione | — | — | 1.0 | — | — | — |
| HIA 1 | 0.5 | 0.1 | 0.2 | 0.2 | 0.3 | 0.3 |
| Perfume | 0 | 0.6 | 0.6 | 0.2 | 0.4 | 0.6 |
| Miscellaneous and water | | | Up to 100% | | | |

What is claimed is:

1. A perfume composition comprising:
  a.) at least 10% by weight of at least one High Impact Accord ("HIA,") perfume ingredient of Class 1, the Class 1 perfume ingredient having:
    (i) a boiling point at 760 mm Hg, of 275° C. or lower;
    (ii) a calculated CLogP of at least 2.0; and
    (iii) an odor detection threshold ("ODT") less than or equal to 50 ppb; and
  b.) at least 30% by weight of at least one High Impact Accord ("HIA") perfume ingredient of Class 2, the Class 2 perfume ingredient having:
    (i) a boiling point at 760 mm Hg, of greater than 275° C.;
    (ii) a calculated CLogP of at least 4.0; and
    (iii) an odor detection threshold ("ODT") less than or equal to 50 ppb;
said perfume composition being encapsulated.

2. A composition according to claim 1, wherein the material used for encapsulating the perfume composition comprises a water-soluble modified starch solid matrix.

3. A composition according to claim 2, wherein the material used for encapsulating the perfume composition comprises a starch raw material that has been modified by treating said starch raw material with octenyl-succinic acid anhydride.

4. A composition according to claim 3, wherein said modified starch comprises a polyhydroxy compound.

5. A composition according to claim 4, wherein said polyhydroxy compound comprises at least 20% by weight of the encapsulation mixture.

6. A laundry and cleaning composition comprising a detersive ingredient and a perfume composition according to claim 1.

7. A process of making the composition of claim 6, comprsing the step of combining the perfume composition of claim 1, by means selected from spraying, dry-mixing, and mixtures thereof, with a detersive ingredient.

8. A composition according to claim 6, wherein said composition further comprises a bleaching system.

9. A composition according to claim 6, wherein said composition is selected from the group consisting of a detergent composition, a hard surface cleaning composition, a dishwashing composition.

10. A method of delivering perfume residuality on surfaces, which comprises the steps of contacting the surface with a composition according to claim 6.

11. A method according to claim 10, wherein said surfaces, are made of mixed types of surfaces.

12. A composition according to claim 1, wherein said Class 1 HIA perfume ingredient is present in an amount of at least 20% by weight of the perfume composition.

13. A composition according to claim 12, wherein said Class 1 HIA perfume ingredient is present in an amount of at least 30% by weight of the perfume composition.

14. A composition according to claim 1, wherein said Class 2 HIA perfume ingredient is present in an amount of at least 40% by weight of the perfume composition.

15. A composition according to claim 14, wherein said Class 2 HIA perfume ingredient is present in an amount of at least 50% by weight of the perfume composition.

* * * * *